US011441008B2

(12) United States Patent
Vucak

(10) Patent No.: US 11,441,008 B2
(45) Date of Patent: Sep. 13, 2022

(54) COMPOSITE POWDER CONTAINING CALCIUM CARBONATE AND HAVING MICROSTRUCTURED PARTICLES

(71) Applicant: Schaefer Kalk GmbH & Co. KG, Diez (DE)

(72) Inventor: Marijan Vucak, Altendiez (DE)

(73) Assignee: Schaefer Kalk GmbH & Co. KG, Diez (DE)

( * ) Notice: Subject to any disclaimer, the term of this patent is extended or adjusted under 35 U.S.C. 154(b) by 0 days.

(21) Appl. No.: 16/330,668

(22) PCT Filed: Sep. 7, 2017

(86) PCT No.: PCT/EP2017/072412
§ 371 (c)(1),
(2) Date: Mar. 5, 2019

(87) PCT Pub. No.: WO2018/046572
PCT Pub. Date: Mar. 15, 2018

(65) Prior Publication Data
US 2019/0211179 A1 Jul. 11, 2019

(30) Foreign Application Priority Data
Sep. 8, 2016 (EP) .................................. 16001954

(51) Int. Cl.
*C08K 3/26* (2006.01)
*A61L 27/44* (2006.01)
*C08J 3/20* (2006.01)
*C09C 1/02* (2006.01)
*C01F 11/18* (2006.01)
*C08J 3/12* (2006.01)
*C09C 1/00* (2006.01)
*A61L 27/58* (2006.01)
*C08K 7/18* (2006.01)

(52) U.S. Cl.
CPC .............. *C08K 3/26* (2013.01); *A61L 27/446* (2013.01); *A61L 27/58* (2013.01); *C01F 11/181* (2013.01); *C01F 11/183* (2013.01); *C08J 3/124* (2013.01); *C08J 3/203* (2013.01); *C08K 7/18* (2013.01); *C09C 1/0081* (2013.01); *C09C 1/021* (2013.01); *C01P 2004/01* (2013.01); *C01P 2004/32* (2013.01); *C01P 2004/61* (2013.01); *C01P 2004/62* (2013.01); *C08J 2367/04* (2013.01); *C08K 2003/265* (2013.01); *C08K 2201/005* (2013.01)

(58) Field of Classification Search
None
See application file for complete search history.

(56) References Cited

U.S. PATENT DOCUMENTS 4,915,884 A 4/1990 Capdeville et al.
5,011,862 A 4/1991 Melber et al.
(Continued)

FOREIGN PATENT DOCUMENTS

DE 4244254 A1 7/1993
EP 0523372 A1 1/1993
(Continued)

OTHER PUBLICATIONS

International Application No. PCT/EP2017/072412, International Search Report, dated Nov. 8, 2017.
International Application No. PCT/EP2017/072412, Written Opinion, dated Nov. 8, 2017.
(Continued)

*Primary Examiner* — Robert T Butcher
(74) *Attorney, Agent, or Firm* — Marshall, Gerstein & Borun LLP

(57) ABSTRACT

A composite powder containing microstructured particles obtainable by means of a method in which large particles are combined with small particles, wherein
the large particles have an average particle diameter within the range from 0.1 μm to 10 mm,
the large particles comprise at least one polymer,
the small particles are arranged on the surface of the large particles and/or distributed inhomogeneously within the large particles,
the small particles comprise sphere-shaped precipitated calcium carbonate particles having an average diameter within the range from 0.05 μm to 50.0 μm, wherein the sphere-shaped calcium carbonate particles are obtainable by means of a method in which
a. a calcium hydroxide suspension is initially charged,
b. carbon dioxide or a carbon dioxide-containing gas mixture is introduced into the suspension from step a. and
c. resultant calcium carbonate particles are separated off, with 0.3% by weight to 0.7% by weight of at least one aminotrisalkylenephosphonic acid being further added.
Preferred application areas of the composite powder encompass its use as additive, especially as polymer additive, as additive substance or starting material for compounding, for the production of components, for applications in medical technology and/or in microtechnology and/or for the production of foamed articles.
The invention therefore also provides components obtainable by selective laser sintering of a composition comprising a composite powder according to the invention, except for implants for uses in the field of neurosurgery, oral surgery, jaw surgery, facial surgery, neck surgery, nose surgery and ear surgery as well as hand surgery, foot surgery, thorax surgery, rib surgery and shoulder surgery.
The invention also provides the sphere-shaped calcium carbonate particles which can advantageously be used to produce the composite particles according to the invention, and the use thereof.

23 Claims, 15 Drawing Sheets

(56) References Cited

U.S. PATENT DOCUMENTS

| | | | |
|---|---|---|---|
| 5,043,017 A | 8/1991 | Passaretti | |
| 5,474,803 A | 12/1995 | Kikuchi et al. | |
| 6,228,161 B1 * | 5/2001 | Drummond | C01F 11/18 106/464 |
| 6,403,219 B1 | 6/2002 | Liao | |
| 2010/0048791 A1 | 2/2010 | Vucak et al. | |
| 2012/0035287 A1 | 2/2012 | Scheer et al. | |
| 2014/0004348 A1 | 1/2014 | Vucak et al. | |
| 2018/0258288 A1 | 9/2018 | Gerard et al. | |
| 2019/0351104 A1 | 11/2019 | Reinauer et al. | |

FOREIGN PATENT DOCUMENTS

| | | |
|---|---|---|
| EP | 0922488 A2 | 6/1999 |
| EP | 2647672 A1 | 10/2013 |
| JP | 62083029 A | 4/1987 |
| JP | 04-004252 A | 1/1992 |
| JP | 07-331038 A | 12/1995 |
| JP | 2008-291254 A | 12/2008 |
| JP | 2010-511751 A | 4/2010 |
| JP | 2016-153354 A | 8/2016 |
| JP | 2019-528841 A | 10/2019 |
| WO | 2008/067531 A2 | 6/2008 |
| WO | WO-2008/122358 A2 | 10/2008 |
| WO | 2012/013349 A2 | 2/2012 |
| WO | WO-2008/122358 A2 | 2/2012 |
| WO | WO-2012/018327 A1 | 2/2012 |
| WO | 2012/073660 A1 | 6/2012 |
| WO | 2012/121296 A1 | 9/2012 |
| WO | WO-2012/126600 A2 | 9/2012 |
| WO | 2013/161751 A1 | 10/2013 |
| WO | 2016/113825 A1 | 7/2016 |
| WO | WO-2016/113285 A1 | 7/2016 |
| WO | 2018/046572 A1 | 3/2018 |
| WO | WO-2018/046127 A1 | 3/2018 |
| WO | WO-2018/046571 A1 | 3/2018 |
| WO | WO-2018/046574 A1 | 3/2018 |

OTHER PUBLICATIONS

*Organikum,* 17th edition, VEB Deutscher Verlag der Wissenschaften, Berlin, 1988, section 2.5.2.1 *"Ausschütteln von Lösungen bzw. Suspensionen"* [shake extraction of solutions or suspensions], pp. 56-57.

*Römpp-Lexikon Chemie* [Römpp's Chemistry Lexicon] / editors Jürgen Falbe; Manfred Regitz. revised by Eckard Amelingmeier; Stuttgart, New York; Thieme; vol. 2: Cm-G; 10th edition (1997); keyword: "surface-active substances".

International Application No. PCT/EP2017/072412, International Preliminary Report on Patentability, dated Mar. 12, 2019.

Kim et al., Mechanical properties and thermal stability of poly(L-lactide)/calcium carbonate composites, J. Appl. Polymer Sci., 109:3087-92 (2008).

Morel et al., Impact of coated calcium carbonate nanofillers and annealing treatments on the microstructure and gas barrier properties of poly(lactide) based nanocomposite films, J. Polymer Sci., 54:649-58 (2016).

Navarro et al., Development and cell response of a new biodegradable composite scaffold for guided bone regeneration, J. Mater. Sci: Materials in Medicine, 15(4):419-22 (Apr. 2004).

* cited by examiner

COMPOSITE POWDER CONTAINING CALCIUM CARBONATE AND HAVING MICROSTRUCTURED PARTICLES

CROSS-REFERENCE TO RELATED APPLICATIONS

This application is a U.S. National Phase of International Patent Application No. PCT/EP2017/072412 filed on Sep. 7, 2017, which claims priority under § 119 to European Patent Application No. 16001954.3, filed on Sep. 8, 2016.

BACKGROUND OF THE INVENTION

The present invention relates to a calcium carbonate-containing composite powder containing microstructured particles, method for production thereof, use thereof and also components obtainable by selective laser sintering, except for implants for uses in the field of neurosurgery, oral surgery, jaw surgery, facial surgery, neck surgery, nose surgery and ear surgery as well as hand surgery, foot surgery, thorax surgery, rib surgery and shoulder surgery.

Calcium carbonate, $CaCO_3$, is a carbonic-acid calcium salt which is nowadays used in many areas of daily life. In particular, it is used as additive or modifier in paper, paints, plastics, inks, adhesives and pharmaceuticals. In plastics, calcium carbonate primarily serves as filler to replace the comparatively expensive polymer.

Composites, too, are already known and refer to a material composed of two or more combined materials that has different material properties compared to its individual components. What are important for the properties of composites are the material properties and the geometry of the components. In particular, size effects are often significant. Combination is generally achieved by integral bonding or form-fitting or a mix of the two.

Furthermore, microstructured composite particles containing calcium salts, especially calcium carbonate, are also already known per se.

For instance, WO 2012/126600 A2 discloses microstructured composite particles obtainable by means of a method in which large particles are combined with small particles, wherein
  the large particles have an average particle diameter within the range from 0.1 μm to 10 mm,
  the average particle diameter of the small particles is not more than 1/10 of the average particle diameter of the large particles,
  the large particles comprise at least one polymer,
  the small particles comprise calcium carbonate,
  the small particles are arranged on the surface of the large particles and/or distributed inhomogeneously within the large particles,
wherein the small particles comprise precipitated calcium carbonate particles having an average particle size within the range from 0.01 μm to 1.0 mm.

Furthermore, WO 2012/126600 A2 describes microstructured composite particles obtainable by means of a method in which large particles are combined with small particles, wherein
  the large particles have an average particle diameter within the range from 0.1 μm to 10 mm,
  the average particle diameter of the small particles is not more than 1/10 of the average particle diameter of the large particles,
  the large particles comprise at least one polymer,
  the small particles comprise at least one calcium salt,
  the small particles are arranged on the surface of the large particles and/or distributed inhomogeneously within the large particles,
wherein the large particles comprise at least one resorbable polyester having a number-average molecular weight within the range from 500 g/mol to 1 000 000 g/mol.

The composite particles shown in WO 2012/126600 A2 are said to be especially suitable as additive, especially as polymer additive, as additive substance or starting material for the production of components, for applications in medical technology and/or in microtechnology and/or for the production of foamed articles. The method of selective laser sintering (SLM method) is mentioned, inter alia, in that document.

However, materials better suited to selective laser sintering are desirable. One disadvantage of the composite particles of WO 2012/126600 A2 is in particular their poor pourability, which can be reduced only partially, even by using pouring aids. Especially for the production of implants, additions of such pouring aids are not advantageous, since they generally adversely affect the properties of the resultant implant, especially its biological compatibility and biodegradability. Furthermore, the poor pourability complicates transport in the laser sintering system.

When producing components by laser sintering using the materials of WO 2012/126600 A2, the following additional problems occur. Although it is possible to carry out sintering of ground composite particles, the surface quality and surface nature as well as the component density of the resultant components is not completely satisfactory. What would be desirable would be in particular a better shrinkage behavior and an improved dimensional stability of the resultant components as well as a better heat-conductivity behavior outside the laser-treated region. Furthermore, a more efficient method of producing components would be desirable.

U.S. Pat. No. 4,915,884 A relates to a method for producing a granular material for water treatment, allowing the production of granules having a specific gravity d and a size t, which can be adjusted independently of one another within the range of $1<d\leq3$ and $0.5\ mm\leq t\leq 10\ mm$ in order to be able to adapt the granules to the treatment type for which the material is intended to be used. The method comprises the formation of a mixture composed of an oxidizable thermoplastic resin having a specific gravity dr less than d and an adjuvant in the form of a powder having a granulometry less than about 200 μm and a specific gravity da meeting the requirement $da>1.7\ d-0.7\ dr$, it being intended that the proportion by weight of the adjuvant pa meet a specific requirement. The mixture is heated into the plastic state, and extruded to form cylindrical strands which are immediately cut into plastic pieces which are shorter than their diameter. The plastic pieces are solidified to form spherical granules and their surface is subjected to oxidation to form hydrophilic sites.

Optionally, a cationic polyelectrolyte is grafted onto the surface of the granules.

The thermoplastic resin used is, for example, HDPE.

The adjuvant used is, for example, calcium carbonate having an average particle size of 30 μm and a specific gravity of 2.71.

The oxidation is, for example, achieved with a mixture composed of sulfuric acid and potassium bichromate.

However, it is not possible to gather from this publication any indication of sphere-shaped calcium carbonate particles.

SUMMARY OF THE INVENTION

Against this background, it is an object of the present invention to show ways of providing a calcium carbonate-containing composite powder having improved properties. In particular, a material having improved laser sintering properties is to be provided, which material has in particular an improved pourability, allows in the case of laser sintering the production of components having improved surface quality and surface nature as well as improved component density, and exhibits in particular better shrinkage behavior and an improved dimensional stability of the resultant components as well as a better heat-conductivity behavior outside the laser-treated region. In addition, a more efficient method of producing components is desired. Lastly, it is also a goal of the present invention to provide particularly advantageous components. Furthermore, solvent-free products which can be used without any difficulties especially in areas with restrictions regarding the presence of solvent residues in the product are striven for. What should be especially highlighted in this context are products for medical technology applications, which must generally be completely solvent-free. Lastly, ways of optimally preventing thermal degradation, especially polymer degradation, during the production of the end products are also sought after.

These objects, and further objects which are not specifically mentioned and which can be directly derived from the above contexts, are achieved by the provision of a composite powder containing microstructured particles having all the features of the present claim 1. The dependent claims which refer back to claim 1 describe particularly expedient use variants of the composite powder. The use claim relates to a particularly expedient application of the composite powder according to the invention. Furthermore, protection is given to a particularly advantageous component obtainable by selective laser sintering of a composition containing a composite powder according to the invention, except for implants for uses in the field of neurosurgery, oral surgery, jaw surgery, facial surgery, neck surgery, nose surgery and ear surgery as well as hand surgery, foot surgery, thorax surgery, rib surgery and shoulder surgery. The invention also provides the sphere-shaped calcium carbonate particles which can advantageously be used to produce the composite particles according to the invention, and the use thereof.

BRIEF DESCRIPTION OF THE DRAWINGS

FIG. 3c: 500 μm doctor blade).

FIG. 4c: 500 μm doctor blade).

FIG. 5c: 500 μm doctor blade). The powder is flowable to a limited extent.

FIG. 6c: 500 μm doctor blade).

FIG. 7c: 500 μm doctor blade).

FIG. 8c: 500 μm doctor blade).

Figure 1:
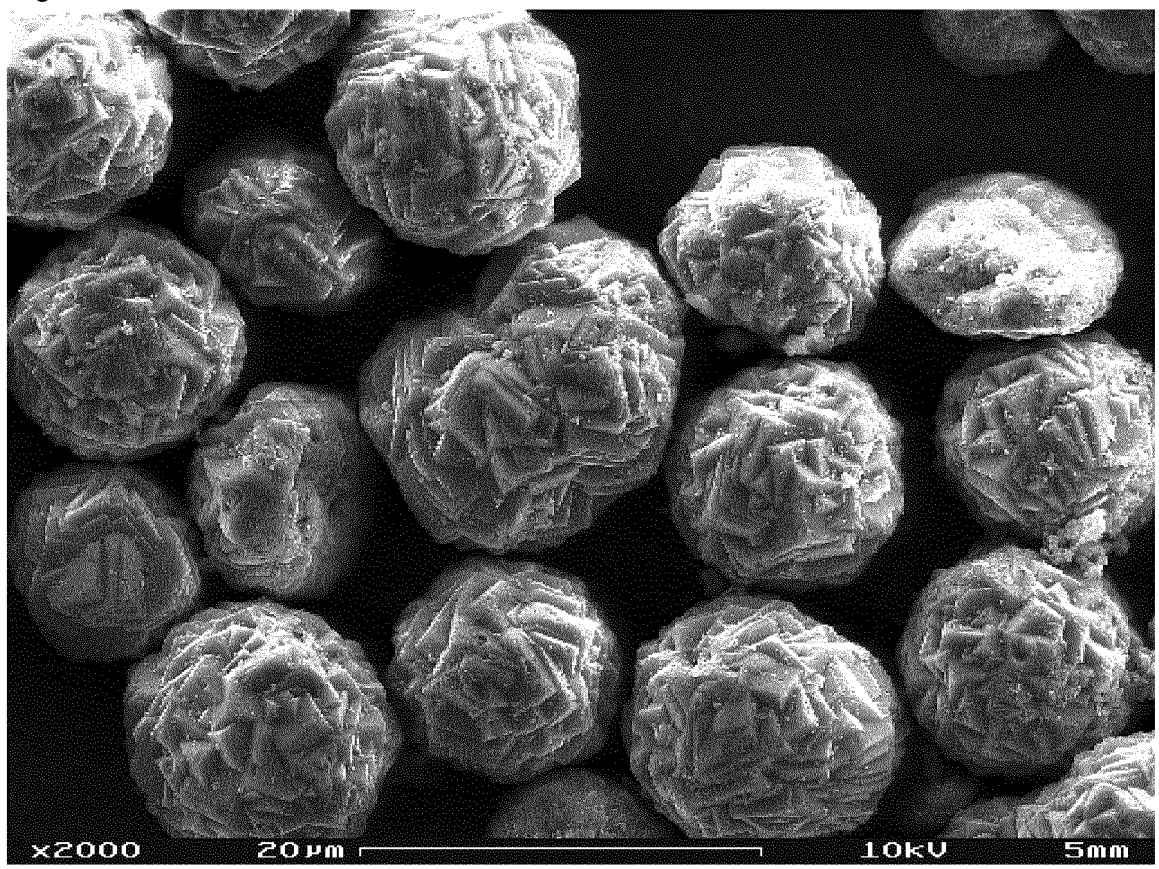
FIG. 1 shows a typical SEM image. The resultant sphere-shaped calcium carbonate particles were separated off and dried by conventional means. They had an average particle diameter of 12 μm.

By providing a composite powder containing microstructured particles obtainable by means of a method in which large particles are combined with small particles, wherein
  the large particles have an average particle diameter within the range from 0.1 μm to 10 mm,
  the large particles comprise at least one polymer,
  the small particles are arranged on the surface of the large particles and/or distributed inhomogeneously within the large particles,
  the small particles comprise sphere-shaped precipitated calcium carbonate particles having an average diameter within the range from 0.05 μm to 50.0 μm, preferably within the range from 2.5 μm to 30.0 μm,
  wherein the sphere-shaped calcium carbonate particles are obtainable by means of a method in which
  a. a calcium hydroxide suspension is initially charged,
  b. carbon dioxide or a carbon dioxide-containing gas mixture is introduced into the suspension from step a. and
  c. resultant calcium carbonate particles are separated off, with 0.3% by weight to 0.7% by weight of at least one aminotrisalkylenephosphonic acid being further added, it is possible to make available, in a not readily foreseeable manner, a calcium carbonate-containing composite powder having improved properties, which are in particular outstandingly suitable for use in laser sintering methods. The composite powder according to the invention has an improved pourability, allows in the case of laser sintering the production of components having improved surface quality and surface nature as well as improved component density. At the same time, the resultant components exhibit in particular a better shrinkage behavior and an improved dimensional stability. Furthermore, a better heat-conductivity behavior outside the laser-treated region can be established.

Furthermore, the composite powder according to the invention allows a more efficient production of components, especially by the laser sintering method. The melt flow of the melt obtainable using the composite powder according to the invention is distinctly increased (improved). In comparison with conventional materials, the composite powder according to the invention is in particular better processable by the SLM method and allows a distinctly better layer structure in the SLM method. The components obtainable by the SLM method using the composite powder according to the invention are distinguished by an extremely high quality and have, in comparison with components produced by the SLM method using conventional materials, distinctly fewer imperfections, a higher component density, preferably greater than 95% and in particular greater than 97%, and a lower porosity. At the same time, the amount of degradation products in the resultant components is distinctly lower and the cell compatibility of the components is extremely high.

The other properties of the components obtainable in this way is excellent, too. The components have very good mechanical properties and a very good pH stability. At the same time, the biological compatibility of the components is distinctly improved. Comparable products are not obtainable using the pure polymers, all the more because corresponding polymer powders that could be processed by the SLM method are not known.

A further advantage of the present invention can be considered that of being able to specifically control and adjust the properties of the composite powder according to the invention, especially the flow properties of the composite powder, via the use amounts and the properties of the large particles and of the small particles, especially via the properties of the calcium carbonate particles, particularly via the particle size of the calcium carbonate particles, and via the amount of calcium carbonate particles. Furthermore, by classification of the composite powder, it is possible for especially the calcium carbonate content of the composite powder and the flow properties of the composite powder to be altered and to be specifically tailored to the particular intended application.

Especially in combination with polylactide as polymer, the following advantages arise according to the invention.

Using the composite powder according to the invention, it is possible to generate degradable implants having controllable resorption kinetics and adjustable mechanical properties. Polylactides, which are preferably present in the composite powder, are biodegradable polymers based on lactic acid. In organisms, polylactides are degraded by hydrolysis. Calcium salts, especially calcium phosphate and calcium carbonate, are mineral materials based on calcium and are degraded in the body by the bone's natural regeneration process. Calcium carbonate has the particularly advantageous property of buffering the acidic environment in the case of polylactide degradation, which environment is sometimes toxic for bone cells. In comparison with calcium phosphate (pH 4), calcium carbonate already buffers at a pH of approx. 7, i.e., close to the physiological value of 7.4. Via the molecular-chain length and the chemical composition of the polymer, especially of the polylactide, it is possible to adjust the time until complete degradation. A similar adjustment is possible for the mechanical properties of the polymer.

The composite powder according to the invention can be processed with the aid of the additive manufacturing process selective laser melting (SLM) to form implant structures. Here, a specific tailoring of material and manufacturing process to one another and to the medical requirements is possible. The utilization of additive manufacturing and of the associated geometrical freedom offers the possibility of providing the implant with an inner and open pore structure which meets the wishes of the surgeon and which ensures that the implant is supplied throughout. Furthermore, implants individually tailored by means of additive manufacturing, as required for the treatment of large-area bone defects in the facial and skull region, can be produced rapidly and economically. The advantage of the composite powder according to the invention for SLM processing is, in particular, that the polymer can be melted by the laser radiation at relatively low temperatures, preferably less than 300° C., and the calcium carbonate particles remain thermally stable at said temperatures. Through tailored synthesis of the composite powder according to the invention, the calcium carbonate particles can thus be embedded homogeneously in the entire volume of the implant in a polylactide matrix without thermal damage due to the laser radiation.

The strength of the implant is determined, firstly, by the polylactide matrix and, secondly, by the morphology of the calcium carbonate particles, and preferably also by the mixture ratio of the components used. Moreover, the implants are bioactive, since they, via the choice of material and the subsequent coating with a growth-stimulating protein (rhBMP-2), induce the surrounding bone tissue in an active manner to build bone and to replace the scaffolding structure (implant).

The major advantages of the implants additively manufactured by means of SLM and composed of the composite powder according to the invention are in particular:

With the use of biodegradable, osteoconductive materials, there is active stimulation of bone growth through the implant and, even in the case of large-area defects, complete degradation is achieved coupled with complete bone regeneration in the bone defect to be treated. Owing to the interconnecting pore structure, the BMP coating can have an active effect in the entire "volume" of the implant.

Inward sprouting of bone tissue: The introduction of a suitable pore structure promotes the inward sprouting of new bone tissue into the implant. By means of the additive manufacturing process, it is possible to introduce a defined pore structure into the components in a reproducible manner.

The proposed solution further offers the advantage of optimally preventing medical complications of long-term implants, of optimally improving the patient's well-being through the avoidance of a permanent foreign-body sensation and—especially in the case of children and juveniles—of optimally realizing a "co-growing" implant.

Optimum buffering: Through the use of calcium carbonate, the acidic degradation of the material polylactide is already buffered at a pH of approx. 7, meaning that the resultant acidic environment surrounding the implant and thus an inflammatory or cytotoxic effect can be avoided. Furthermore, degradation processes of the polymer, especially of the lactic acid polymer, are optimally suppressed.

High strength: The SLM process generates a complete fused composite and thus a high component density and strength, the result being that it is also possible to treat large-area defects with individually tailored implants composed of a biodegradable material and open pore structure.

Furthermore, the products according to the invention can be produced without the use of conventional solvents and are therefore preferably distinguished by this "freedom from solvent". This allows their use especially in areas with restrictions regarding the presence of solvent residues in the product, since the products according to the invention can be used without any difficulties here. What should be especially highlighted in this context are medical technology applications, which must generally be completely solvent-free. Lastly, the composite powder according to the invention can be processed further in a comparatively simple manner to form the desired end products. A thermal degradation, especially polymer degradation, during the production of the end products is optimally prevented.

Accordingly, the present invention provides composite powders containing microstructured particles obtainable by means of a method in which large particles are combined with small particles.

In the present invention, the microscopic properties of a material are referred to as microstructure. They include the resolvable fine structure and the grain structure. They are not present in liquids and gases. In this case, the individual atoms or molecules are present in a nonordered state. Amorphous solids have in most cases a structural short-range order in the region of adjacent atoms, but not a long-range order. By contrast, crystalline solids have an ordered lattice structure not only in the short-range region, but also in the long-range region.

Within the context of the present invention, the large particles comprise at least one polymer, which polymer is fundamentally not subject to any further restrictions. However, the polymer is preferably a thermoplastic polymer, expediently a biopolymer, a rubber, especially natural rubber or synthetic rubber, and/or a polyurethane.

In this context, the term "thermoplastic polymer" refers to a plastic which can be deformed (thermoplastically) within a certain temperature range, preferably within the range from 25° C. to 350° C. This process is reversible, i.e., it can be repeated as often as desired through cooling and reheating right into the molten state, so long as so-called thermal decomposition of the material does not commence as a result of overheating. This distinguishes thermoplastic polymers from the thermosets and elastomers.

The term "biopolymer" refers to a material which consists of biogenic raw materials (renewable raw materials) and/or is biodegradable (biogenic and/or biodegradable polymer). Said term thus covers biobased biopolymers which are biodegradable or else not biodegradable as well as petroleum-based polymers which are biodegradable. This provides a delimitation with respect to the conventional, petroleum-based materials or plastics which are not biodegradable, such as, for example, polyethylene (PE), polypropylene (PP) and polyvinyl chloride (PVC).

The term "rubber" refers to a high-molecular-weight, uncrosslinked polymeric material having rubber-elastic properties at room temperature (25° C.). At higher temperatures or under the influence of deformation forces, a rubber exhibits an increasing viscous flow and thus allows its reshaping under suitable conditions.

Rubber-elastic behavior is characterized by a relatively low shear modulus with a rather low temperature dependence. It is caused by changes in entropy. As a result of stretching, the rubber-elastic material is forced into a more ordered configuration, which leads to a decrease in entropy. After removal of the force, the polymers therefore return to their original position and entropy goes back up.

The term "polyurethane" (PU, DIN [German Institute for Standardization] abbreviation: PUR) refers to a plastic or a synthetic resin, each of which arises from the polyaddition reaction of diols or polyols with polyisocyanates. Characteristic of a polyurethane is the urethane group.

Within the context of the present invention, particular preference is given to using thermoplastic polymers. In this connection, particularly suitable polymers include the following polymers: acrylonitrile-ethylene-propylene-(diene)-styrene copolymer, acrylonitrile-methacrylate copolymer, acrylonitrile-methyl methacrylate copolymer, acrylonitrile-chlorinated polyethylene-styrene copolymer, acrylonitrile-butadiene-styrene copolymer, acrylonitrile-ethylene-propylene-styrene copolymer, aromatic polyesters, acrylonitrile-styrene-acrylic ester copolymer, butadiene-styrene copolymer, cellulose acetate, cellulose acetate butyrate, cellulose acetate propionate, hydrogenated cellulose, carboxymethylcellulose, cellulose nitrate, cellulose propionate, cellulose triacetate, polyvinyl chloride, ethylene-acrylic acid copolymer, ethylene-butyl acrylate copolymer, ethylene-chlorotrifluoroethylene copolymer, ethylene-ethyl acrylate copolymer, ethylene-methacrylate copolymer, ethylene-methacrylic acid copolymer, ethylene-tetrafluoroethylene copolymer, ethylene-vinyl alcohol copolymer, ethylene-butene copolymer, ethylcellulose, polystyrene, polyfluoroethylenepropylene, methyl methacrylate-acrylonitrile-butadiene-styrene copolymer, methyl methacrylate-butadiene-styrene copolymer, methylcellulose, polyamide 11, polyamide 12, polyamide 46, polyamide 6, polyamide 6-3-T, polyamide 6-terephthalic acid copolymer, polyamide 66, polyamide 69, polyamide 610, polyamide 612, polyamide 61, polyamide MXD6, polyamide PDA-T, polyamide, polyaryl ether, polyaryl ether ketone, polyamide imide, polyacrylamide, polyaminobismaleimide, polyarylates, polybutene-1, polybutyl acrylate, polybenzimidazole, polybismaleimide, polyoxadiazobenzimidazole, polybutylene terephthalate, polycarbonate, polychlorotrifluoroethylene, polyethylene, polyester carbonate, polyaryl ether ketone, polyether ether ketone, polyether imide, polyether ketone, polyethylene oxide, polyaryl ether sulfone, polyethylene terephthalate, polyimide, polyisobutylene, polyisocyanurate, polyimide sulfone, polymethacrylimide, polymethacrylate, poly-4-methyl-1-pentene, polyacetal, polypropylene, polyphenylene oxide, polypropylene oxide, polyphenylene sulfide, polyphenylene sulfone, polystyrene, polysulfone, polytetrafluoroethylene, polyurethane, polyvinyl acetate, polyvinyl alcohol, polyvinyl butyral, polyvinyl chloride, polyvinylidene chloride, polyvinylidene fluoride, polyvinyl fluoride, polyvinyl methyl ether, polyvinylpyrrolidone, styrene-butadiene copolymer, styrene-isoprene copolymer, styrene-maleic anhydride copolymer, styrene-maleic anhydride-butadiene copolymer, styrene-methyl methacrylate copolymer, styrene-methylstyrene copolymer, styrene-acrylonitrile copolymer, vinyl chloride-ethylene copolymer, vinyl chloride-methacrylate copolymer, vinyl chloride-maleic anhydride copolymer, vinyl chloride-maleimide copolymer, vinyl chloride-methyl methacrylate copolymer, vinyl chloride-octylacrylate copolymer, vinyl chloride-vinyl acetate copolymer, vinyl chloride-vinylidene chloride copolymer and vinyl chloride-vinylidene chloride-acrylonitrile copolymer.

Furthermore, the use of the following rubbers is also particularly advantageous: naturally occurring polyisoprene, especially cis-1,4-polyisoprene (natural rubber; NR) and trans-1,4-polyisoprene (gutta-percha), particularly natural rubber; nitrile rubber (copolymer of butadiene and acrylonitrile; poly(acrylonitrile-co-1,3-butadiene; NBR; so-called Buna-N rubber); butadiene rubber (polybutadiene; BR); acrylic rubber (polyacrylic rubber; ACM, ABR); fluororubber (FPM); styrene-butadiene rubber (copolymer of styrene and butadiene; SBR); styrene-isoprene-butadiene rubber (copolymer of styrene, isoprene and butadiene; SIBR); polybutadiene; synthetic isoprene rubber (polyisoprene; IR); ethylene-propylene rubber (copolymer of ethylene and propylene; EPM); ethylene-propylene-diene rubber (terpolymer of ethylene, propylene and a diene component; EPDM); butyl rubber (copolymer of isobutylene and isoprene; IIR); ethylene-vinyl acetate rubber (copolymer of ethylene and vinyl acetate; EVM); ethylene-methyl acrylate rubber (copolymer of ethylene and methyl acrylate; AEM); epoxy rubber, such as polychloromethyloxirane (epichlorohydrin polymer; CO), ethylene oxide (oxirane)-chloromethyloxirane (epichlorohydrin polymer; ECO), epichlorohydrin-ethylene oxide-allyl glycidyl ether terpolymer (GECO), epichlorohydrin-allyl glycidyl ether copolymer (GCO) and propylene oxide-allyl glycidyl ether copolymer (GPO); polynorbornene rubber (polymer of bicyclo[2.2.1]hept-2-ene (2-norbornene); PNR); polyalkenylene (polymer of cycloolefins); silicone rubber (Q), such as silicone rubber only with methyl substituents on the polymer chain (MQ; e.g., dimethylpolysiloxane), silicone rubber with methylvinyl and vinyl substituent groups on the polymer chain (VMQ), silicone rubber with phenyl and methyl substituents on the polymer chain (PMQ), silicone rubber with fluoro and methyl groups on the polymer chain (FMQ), silicone rubber with fluoro, methyl and vinyl substituents on the polymer chain (FVMQ); polyurethane rubber; thiokol rubber; halobutyl rubber, such as bromobutyl rubber (BIIR) and chlorobutyl rubber (CIIR); chloropolyethylene (CM); chlorosulfonyl polyethylene (CSM); hydrogenated nitrile rubber (HNBR); and polyphosphazene.

Particularly preferred nitrile rubbers include random terpolymers of acrylonitrile, butadiene and a carboxylic acid, such as methacrylic acid. In this context, the nitrile rubber preferably comprises, based on the total weight of the polymer, the following main components: 15.0% by weight to 42.0% by weight of acrylonitrile polymer; 1.0% by weight to 10.0% by weight of carboxylic acid and the rest is predominantly butadiene (e.g., 38.0% by weight to 75.0% by weight). Typically, the composition is: 20.0% by weight to 40.0% by weight of acrylonitrile polymer, 3.0% by weight to 8.0% by weight of carboxylic acid and 40.0% by weight to 65.0% by weight or 67.0% by weight are butadiene. Particularly preferred nitrile rubbers include a terpolymer of acrylonitrile, butadiene and a carboxylic acid, in which terpolymer the acrylonitrile content is less than 35.0% by weight and the carboxylic acid content is less than 10.0% by weight, with the butadiene content corresponding to the remaining rest. Even more preferred nitrile rubbers can comprise the following amounts: 20.0% by weight to 30.0% by weight of acrylonitrile polymer, 4.0% by weight to 6.0% by weight of carboxylic acid and the rest is predominantly butadiene.

The use of nitrogenous polymers, especially of polyamides, is particularly favorable within the context of the present invention. Particular preference is given to polyamide 11, polyamide 12, polyamide 46, polyamide 6, polyamide 6-3-T, polyamide 6-terephthalic acid copolymer, polyamide 66, polyamide 69, polyamide 610, polyamide 612, polyamide 61, polyamide MXD6 and/or polyamide PDA-T, especially polyamide 12.

Furthermore, ultra-high-molecular-weight polyethylenes (UHMWPE) are also particularly advantageous for the purposes of the present invention, especially those having an average molar mass greater than 1000 kg/mol, preferably greater than 2000 kg/mol, particularly preferably greater than 3000 kg/mol and in particular greater than 5000 kg/mol. In this connection, the average molecular weight is favorably not more than 10 000 kg/mol. The density of particularly suitable ultra-high-molecular-weight polyethylenes is within the range of 0.94-0.99 g/cm$^3$. The crystallinity of particularly suitable ultra-high-molecular-weight polyethylenes is within the range from 50% to 90%. The tensile strength of particularly suitable ultra-high-molecular-weight polyethylenes is within the range from 30 N/mm$^2$ to 50 N/mm$^2$. The tensile elastic modulus of particularly suitable ultra-high-molecular-weight polyethylenes is within the range from 800 N/mm$^2$ to 2700 N/mm$^2$. The melting range of particularly suitable ultra-high-molecular-weight polyethylenes is within the range from 135° C. to 155° C.

Furthermore, the use of resorbable polymers is also particularly expedient. The term "resorption" (Latin: resorbere="absorb") is understood to mean the uptake of substances in biological systems, especially into the human organism. Of interest here are especially those materials which can be used for the production of resorbable implants.

Resorbable polymers which are particularly preferred according to the invention comprise repeat units of lactic acid, of hydroxybutyric acid and/or of glycolic acid, preferably of lactic acid and/or of glycolic acid, in particular of lactic acid. Polylactic acids are particularly preferred in this connection.

"Polylactic acid" (polylactides) are understood here to mean polymers which are constructed from lactic acid units. Such polylactic acids are usually produced by condensation of lactic acids, but are also obtained in the ring-opening polymerization of lactides under suitable conditions.

Resorbable polymers which are particularly suitable according to the invention include poly(glycolide-co-L-lactide), poly(L-lactide), poly(L-lactide-co-ε-caprolactone), poly(L-lactide-co-glycolide), poly(L-lactide-co-D,L-lactide), poly(D,L-lactide-co-glycolide) and poly(dioxanone), with lactic acid polymers, especially poly-D-, poly-L- or poly-D,L-lactic acids, particularly poly-L-lactic acids (PLLA) and poly-D,L-lactic acids, being very particularly preferred according to the invention, with especially the use of poly-L-lactic acids (PLLA) being very particularly advantageous.

According to the invention, poly-L-lactic acid (PLLA) preferably has the following structure

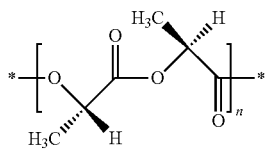

where n is a whole number, preferably greater than 10.

Poly-D,L-lactic acid preferably has the following structure

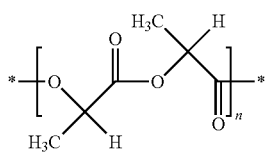

where n is a whole number, preferably greater than 10.

Lactic acid polymers suitable for the purposes of the present invention are, for example, commercially available from Evonik Nutrition & Care GmbH under the trade names Resomer® GL 903, Resomer® L 206 S, Resomer® L 207 S, Resomer® R 208 G, Resomer® L 209 S, Resomer® L 210, Resomer® L 210 S, Resomer® LC 703 S, Resomer® LG 824 S, Resomer® LG 855 S, Resomer® LG 857 S, Resomer® LR 704 S, Resomer® LR 706 S, Resomer® LR 708, Resomer® LR 927 S, Resomer® RG 509 S and Resomer® X 206 S.

Resorbable polymers which are particularly advantageous for the purposes of the present invention, these being preferably resorbable polyesters, by preference lactic acid polymers, particularly preferably poly-D-, poly-L- or poly-D,L-lactic acids and in particular poly-L-lactic acids, have a number-average molecular weight (Mn), preferably determined by gel-permeation chromatography against narrow-distribution polystyrene standards or by end-group titration, greater than 500 g/mol, preferably greater than 1000 g/mol, particularly preferably greater than 5000 g/mol, expediently greater than 10 000 g/mol and in particular greater than 25 000 g/mol. On the other hand, the number average of preferred resorbable polymers is less than 1 000 000 g/mol, expediently less than 500 000 g/mol, favorably less than 100 000 g/mol and in particular not more than 50 000 g/mol. A number-average molecular weight within the range from 500 g/mol to 50 000 g/mol has been found to very particularly effective within the context of the present invention.

The weight-average molecular weight (Mw) of preferred resorbable polymers, these being by preference resorbable polyesters, favorably lactic acid polymers, particularly preferably poly-D-, poly-L- or poly-D,L-lactic acids and in particular poly-L-lactic acids, preferably determined by gel-permeation chromatography against narrow-distribution polystyrene standards, is by preference within the range from 750 g/mol to 5 000 000 g/mol, preferably within the range from 750 g/mol to 1 000 000 g/mol, particularly preferably within the range from 750 g/mol to 500 000 g/mol and in particular within the range from 750 g/mol to 250 000 g/mol, and the polydispersity of said polymers is favorably within the range from 1.5 to 5.

The inherent viscosity of particularly suitable resorbable polymers, these being preferably lactic acid polymers, particularly preferably poly-D-, poly-L- or poly-D,L-lactic acids and in particular poly-L-lactic acids, measured in chloroform at 25° C. and 0.1% polymer concentration, is within the range from 0.3 dL/g to 8.0 dL/g, preferably within the range from 0.5 dL/g to 7.0 dL/g, particularly preferably within the range from 0.8 dL/g to 2.0 dL/g and in particular within the range from 0.8 dL/g to 1.2 dL/g.

Furthermore, the inherent viscosity of particularly suitable resorbable polymers, these being preferably lactic acid polymers, particularly preferably poly-D-, poly-L- or poly-D,L-lactic acids and in particular poly-L-lactic acids, measured in hexafluoro-2-propanol at 30° C. and 0.1% polymer concentration, is within the range from 1.0 dL/g to 2.6 dL/g and in particular within the range from 1.3 dL/g to 2.3 dL/g.

Furthermore, what are extremely advantageous within the context of the present invention are polymers, favorably thermoplastic polymers, preferably lactic acid polymers, particularly preferably poly-D-, poly-L- or poly-D,L-lactic acids and in particular poly-L-lactic acids, having a glass transition temperature greater than 20° C., favorably greater than 25° C., preferably greater than 30° C., particularly preferably greater than 35° C. and in particular greater than 40° C. Within the context of a very particularly preferred embodiment of the present invention, the glass transition temperature of the polymer is within the range from 35° C. to 70° C., favorably within the range from 55° C. to 65° C. and in particular within the range from 60° C. to 65° C.

Furthermore, what are particularly suitable are polymers, favorably thermoplastic polymers, preferably lactic acid polymers, particularly preferably poly-D-, poly-L- or poly-D,L-lactic acids and in particular poly-L-lactic acids, having a melting temperature greater than 50° C., favorably of at least 60° C., preferably of greater than 150° C., particularly preferably within the range from 130° C. to 210° C. and in particular within the range from 175° C. to 195° C.

In this connection, the glass temperature and the melting temperature of the polymer is preferably ascertained by means of differential scanning calorimetry (DSC for short). The following procedure has been found to very particularly effective in this context:

Performance of the DSC measurement under nitrogen on a Mettler-Toledo DSC 30S. The calibration is preferably done using indium. The measurements are preferably carried out under dry, oxygen-free nitrogen (flow rate: preferably 40 ml/min). The sample weight is preferably chosen between 15 mg and 20 mg. The samples are first heated from 0° C. to preferably a temperature above the melting temperature of the polymer under investigation, then cooled to 0° C. and heated a second time from 0° C. to the stated temperature at a heating rate of 10° C./min.

Thermoplastic polymers which are very particularly preferred are polyamides, UHMWPE and resorbable polymers, particularly resorbable polyesters, such as polybutyric acid, polyglycolic acid (PGA), lactic acid polymers (PLA) and lactic acid copolymers, with lactic acid polymers and lactic acid copolymers, in particular poly-L-lactide, poly-D,L-lactide and copolymers of D,L-PLA and PGA, having been found to be very particularly effective according to the invention.

For the goals of the present invention, what are very particularly suitable are especially the following polymers:
1) poly-L-lactide (PLLA), preferably having an inherent viscosity within the range from 0.5 dL/g to 2.5 dL/g, favorably within the range from 0.8 dL/g to 2.0 dL/g and in particular within the range from 0.8 dL/g to 1.2 dL/g (measured in each case at 0.1% in chloroform at 25° C.), preferably having a glass transition temperature within the range from 60° C. to 65° C., further preferably having a melting temperature within the range from 180° C. to 185° C., further preferably ester-terminated;
2) poly(D,L-lactide), preferably having an inherent viscosity within the range from 1.0 dL/g to 3.0 dL/g, favorably within the range from 1.5 dL/g to 2.5 dL/g and in particular within the range of 1.8-2.2 dL/g (measured in each case at 0.1% in chloroform at 25° C.), preferably having a glass transition temperature within the range from 55° C. to 60° C., with the best results being achieved using a poly-L-lactide which preferably has an inherent viscosity within the range from 0.5 dL/g to 2.5 dL/g, favorably within the range from 0.8 dL/g to 2.0 dL/g and in particular within the range from 0.8 dL/g to 1.2 dL/g (measured in each case at 0.1% in chloroform at 25° C.), preferably has a glass transition temperature within the range from 60° C. to 65° C., further preferably has a melting temperature within the range from 180° C. to 185° C. and is further preferably ester-terminated.

Within the context of the present invention, the small particles (second material) usable for the production of the composite powder according to the invention comprise sphere-shaped precipitated calcium carbonate particles. In contrast to other known shapes from the prior art, the calcium carbonate particles are thus not, for example, constructed from needles, rhombohedrons or scalenohedrons (precipitated calcium carbonate; PCC) or from irregularly shaped particles (ground calcium carbonate; GCC), but from sphere-shaped precipitated particles, which are preferably predominantly present as individual particles. However, relatively small deviations from the perfect sphere shape are accepted, provided that the properties of the particles, especially their dispersibility, are not fundamentally changed. For instance, the surface of the particles can have occasional imperfections or additional deposits.

According to the invention, the term "sphere-shaped precipitated calcium carbonate particles" also encompasses fragments of sphere-shaped particles, which are, for example, obtainable by grinding of the calcium carbonate. However, the proportion of the sphere fragments is by preference less than 95%, preferably less than 75%, particularly preferably less than 50% and in particular less than 25%, based in each case on the total amount of sphere-shaped precipitated calcium carbonate.

The average diameter of the sphere-shaped calcium carbonate particles is within the range from 0.05 µm to 50.0 µm, especially within the range from 2.5 µm to 30.0 µm. In this connection, the average diameter is expediently greater than 2.5 µm, favorably greater than 3.0 µm, by preference greater than 4.0 µm, expediently greater than 5.0 µm, expediently greater than 6.0 µm, preferably greater than 7.0 µm, particularly preferably greater than 8.0 µm, yet more preferably greater than 9.0 µm, very particularly preferably greater than 10.0 µm, yet more preferably greater than 11.0 µm, particularly greater than 12.0 µm and in particular greater than 13.0 µm. Furthermore, the average particle diameter is expediently less than 30.0 µm, favorably less than 20.0 µm, preferably less than 18.0 µm, particularly preferably less than 16.0 µm and in particular less than 14.0 µm.

Within the context of the present invention, the average diameter of the calcium carbonate particles is expediently ascertained by evaluation of scanning electron micrographs (SEM images), with preferably only particles of a size of at least 0.01 µm being taken into consideration and a number average being formed over preferably at least 20 and particularly preferably at least 40 particles. Furthermore, sedimentation analysis methods have also been found to be particularly effective, with the use of a Sedigraph 5100 (Micromeritics GmbH) being particularly advantageous in this context.

The size distribution of the calcium carbonate particles is expediently comparatively narrow and preferably such that at least 90.0% by weight of all calcium carbonate particles have a particle diameter within the range of average particle diameter −30% to average particle diameter +30%.

The shape factor of the calcium carbonate particles, defined here as the quotient formed from minimum particle diameter and maximum particle diameter, is expediently greater than 0.90 and particularly preferably greater than 0.95 for at least 90% and favorably for at least 95% of all particles. In this context, what are taken into consideration are preferably only particles having a particle size within the range from 0.1 µm to 50.0 µm, especially within the range from 0.1 µm to 30.0 µm.

The calcium carbonate particles are favorably distinguished by a comparatively low water content. Based on their total weight, they have expediently a water content (residual moisture at 200° C.) of not more than 5.0% by weight, by preference of not more than 2.5% by weight, preferably of not more than 1.0% by weight, particularly preferably of not more than 0.5% by weight, yet more preferably less than 0.4% by weight, expediently less than 0.3% by weight, favorably less than 0.2% by weight and in particular within the range from >0.1% by weight to <0.2% by weight.

Within the context of the present invention, the water content of the calcium salt particles, especially of the calcium carbonate particles, is preferably ascertained by means of thermogravimetry or by means of an infrared rapid dryer, for example MA35 or MA45 from Sartorius or halogen moisture analyzer HB43 from Mettler, with the measurement being carried out preferably under nitrogen (nitrogen flow rate preferably 20 ml/min) and expediently over the temperature range from 40° C. or lower to 250° C. or higher. Furthermore, the measurement is preferably done at a heating rate of 10° C./min.

The specific surface area of the calcium carbonate particles is by preference less than 3.0 m$^2$/g, preferably less than 2.0 m$^2$/g and in particular less than 1.5 m$^2$/g. Furthermore, the specific surface area is favorably greater than 0.25 m$^2$/g, preferably greater than 0.5 m$^2$/g and in particular greater than 0.75 m$^2$/g.

Within the context of a particularly preferred variant of the present invention, the calcium carbonate particles, especially the precipitated calcium carbonate particles, are preferably sphere-shaped and substantially amorphous. Here, the term "amorphous" refers to those calcium carbonate forms in which the atoms form at least in part an irregular pattern instead of ordered structures and therefore have only a short-range order, but not a long-range order. What can be distinguished therefrom are crystalline forms of the calcium carbonate, such as, for example, calcite, vaterite and aragonite, in which crystalline forms the atoms have both a short-range and a long-range order.

Within the context of this preferred variant of the present invention, the presence of crystalline constituents is, however, not categorically ruled out. By preference, the proportion of crystalline calcium carbonate is, however, less than 50% by weight, particularly preferably less than 30% by weight, very particularly preferably less than 15% by weight and in particular less than 10% by weight. Within the context of a particularly preferred variant of the present invention, the proportion of crystalline calcium carbonate is less than 8.0% by weight, preferably less than 6.0% by weight, expediently less than 4.0% by weight, particularly preferably less than 2.0% by weight, very particularly preferably less than 1.0% by weight and in particular less than 0.5% by weight, based in each case on the total weight of the calcium carbonate.

For the ascertainment of the amorphous and the crystalline fractions, X-ray diffraction with an internal standard, preferably quartz, in conjunction with Rietveld refinement has been found to be very particularly effective.

Within the context of this preferred embodiment of the present invention, the preferably amorphous calcium carbonate particles are favorably stabilized by at least one substance, especially at least one surface-active substance, which is preferably arranged on the surface of the preferably sphere-shaped calcium carbonate particles. Within the context of the present invention, "surface-active substances" refer expediently to organic compounds which strongly build up from their solution at interfaces (water/calcium carbonate particles) and thereby lower the surface tension, preferably measured at 25° C. For further details, reference is made to the technical literature, especially to Römpp-Lexikon Chemie [Römpp's Chemistry Lexicon]/editors Jürgen Falbe; Manfred Regitz. revised by Eckard Amelingmeier; Stuttgart, N.Y.; Thieme; volume 2: Cm-G; 10th edition (1997); keyword: "surface-active substances".

By preference, the substance, especially the surface-active substance, has a molar mass greater than 100 g/mol, preferably greater than 125 g/mol and in particular greater than 150 g/mol, and satisfies the formula R—X$_n$.

In this connection, the radical R represents a radical comprising at least 1, by preference at least 2, preferably at least 4, particularly preferably at least 6 and in particular at least 8 carbon atoms, and preferably represents an aliphatic or cycloaliphatic radical which can optionally comprise further radicals X and which can optionally have one or more ether linkages.

The radical X represents a group comprising at least one oxygen atom and at least one carbon atom, sulfur atom, phosphorus atom and/or nitrogen atom, preferably at least one phosphorus atom and/or at least one carbon atom. Particular preference is given to the following groups:

carboxylic acid groups ~COOH,
carboxylate groups ~COO⁻,
sulfonic acid groups ~SO$_3$H,
sulfonate groups ~SO$_3^-$,
hydrogensulfate groups ~OSO$_3$H,
sulfate groups ~OSO$_3^-$,
phosphonic acid groups ~PO$_3$H$_2$,
phosphonate groups ~PO$_3$H$^-$, ~PO$_3^{2-}$,
amino groups ~NR$^1$R$^2$ and
ammonium groups ~N$^+$R$^1$R$^2$R$^3$,
especially carboxylic acid groups, carboxylate groups, phosphonic acid groups and phosphonate groups.

In this context, the radicals R$^1$, R$^2$ and R$^3$ represent, independently of one another, hydrogen or an alkyl group having 1 to 5 carbon atoms. One of the radicals R$^1$, R$^2$ and R$^3$ can also be a radical R.

Preferred counterions for the abovementioned anions are metal cations, especially alkali metal cations, preferably Na$^+$ and K$^+$, and also ammonium ions.

Preferred counterions for the abovementioned cations are hydroxyl ions, hydrogencarbonate ions, carbonate ions, hydrogensulfate ions, sulfate ions and halide ions, especially chloride ions and bromide ions.

n represents a preferably whole number within the range from 1 to 20, preferably within the range from 1 to 10 and in particular within the range from 1 to 5.

Substances particularly suitable for the purposes of the present invention encompass alkylcarboxylic acids, alkyl carboxylates, alkylsulfonic acids, alkyl sulfonates, alkyl sulfates, alkyl ether sulfates having preferably 1 to 4 ethylene glycol ether units, fatty alcohol ethoxylates having preferably 2 to 20 ethylene glycol ether units, alkylphenol ethoxylates, optionally substituted alkylphosphonic acids, optionally substituted alkyl phosphonates, sorbitan fatty acid esters, alkylpolyglucosides, N-methylglucamides, homopolymers and copolymers of acrylic acid and also their corresponding salt forms and block copolymers.

A first group of very particularly advantageous substances are optionally substituted alkylphosphonic acids, especially aminotris(methylenephosphonic acid), 1-hydroxyethylene-(1,1-diphosphonic acid), ethylenediamine tetra(methylenephosphonic acid), hexamethylenediamine tetra(methylenephosphonic acid), diethylenetriamine penta (methylenephosphonic acid), and optionally substituted alkyl phosphonates, especially of the abovementioned acids. These compounds are known as multifunctional sequestrants for metal ions and scale inhibitors.

Furthermore, homopolymers and copolymers, preferably homopolymers, of acrylic acid and their corresponding salt forms have also been found to be particularly effective, especially those having a weight-average molecular weight within the range of 1000 g/mol-10 000 g/mol.

Furthermore, the use of block copolymers, preferably of doubly hydrophilic block copolymers, especially of polyethylene oxide or polypropylene oxide, is particularly favorable.

The proportion of preferably surface-active substances can be, in principle, freely chosen and specifically adjusted for the particular application. However, it is preferably within the range from 0.1% by weight to 5.0% by weight, in particular within the range from 0.3% by weight to 1.0% by weight, based on the calcium carbonate content of the particles.

The preferably sphere-shaped, preferably amorphous calcium carbonate particles can be produced in a manner known per se, for example by hydrolysis of dialkyl carbonate or of alkylene carbonate in a solution comprising calcium cations.

The production of unstabilized, sphere-shaped calcium carbonate particles is, for example, described in detail in the patent application WO 2008/122358, the disclosure of which, especially with regard to particularly expedient variants of the production of such unstabilized, sphere-shaped calcium carbonate particles, is hereby explicitly incorporated by reference.

The hydrolysis of the dialkyl carbonate or of the alkylene carbonate is expediently carried out in the presence of a hydroxide.

Substances which comprise Ca$^{2+}$ ions and are preferred for the purposes of the present invention are calcium halides, preferably CaCl$_2$, CaBr$_2$, in particular CaCl$_2$, and also calcium hydroxide. Within the context of a first particularly preferred embodiment of the present invention, CaCl$_2$ is used. In a further particularly preferred embodiment of the present invention, Ca(OH)$_2$ is used.

Within the context of a first particularly preferred embodiment of the present invention, a dialkyl carbonate is used. Particularly suitable dialkyl carbonates comprise 3 to 20, preferably 3 to 9, carbon atoms, especially dimethyl carbonate, diethyl carbonate, di-n-propyl carbonate, diisopropyl carbonate, di-n-butyl carbonate, di-sec-butyl carbonate and di-tert-butyl carbonate, with very particular preference being given to dimethyl carbonate in this context.

In a further particularly preferred embodiment of the present invention, an alkylene carbonate is reacted. Particularly expedient alkylene carbonates comprise 3 to 20, preferably 3 to 9, particularly preferably 3 to 6, carbon atoms and include especially those compounds comprising a ring composed of 3 to 8, preferably 4 to 6, in particular 5, atoms, with preferably 2 oxygen atoms and otherwise carbon atoms. Propylene carbonate (4-methyl-1,3-dioxolane) has been found to be very particularly effective in this context.

Alkali metal hydroxides, especially NaOH, and calcium hydroxide have been found to be particularly suitable as hydroxide. Within the context of a first particularly preferred embodiment of the present invention, NaOH is used. Within the context of a further particularly preferred embodiment of the present invention, Ca(OH)$_2$ is used.

Furthermore, the molar ratio of Ca$^{2+}$, preferably of calcium chloride, to OH$^-$, preferably alkali metal hydroxide, in the reaction mixture is preferably greater than 0.5:1 and particularly preferably within the range from >0.5:1 to 1:1, in particular within the range from 0.6:1 to 0.9:1.

The molar ratio of Ca$^{2+}$, preferably of calcium chloride, to dialkyl carbonate and/or alkylene carbonate in the reaction mixture is favorably within the range from 0.9:1.5 to 1.1:1 and particularly preferably within the range from 0.95:1 to 1:0.95. Within the context of a very particularly expedient variant of the present invention, the dialkyl carbonate and/or the alkylene carbonate and the Ca$^{2+}$, especially the calcium chloride, are used equimolarly.

Within the context of a first very particularly preferred variant of the present invention, Ca(OH)$_2$ is not used as OH$^-$ source. In this connection, the components for the reaction are favorably used in the following concentrations:
a) Ca$^{2+}$: >10 mmol/L to 50 mmol/L, preferably 15 mmol/L to 45 mmol/L, in particular 17 mmol/L to 35 mmol/L;
b) Dialkyl carbonate and/or
   alkylene carbonate: >10 mmol/L to 50 mmol/L, preferably 15 mmol/L to 45 mmol/L, in particular 17 mmol/L to 35 mmol/L;

c) OH⁻: 20 mmol/L to 100 mmol/L, preferably 20 mmol/L to 50 mmol/L, particularly preferably 25 mmol/L to 45 mmol/L, in particular 28 mmol/L to 35 mmol/L.

In this connection, the respective specified concentrations are based on the concentrations of the stated components in the reaction mixture.

Within the context of a further very particularly preferred variant of the present invention, $Ca(OH)_2$, preferably lime milk, in particular saturated lime milk, is used as OH⁻ source. In this connection, the components for the reaction are favorably used in the following concentrations:

a) $Ca(OH)_2$: >5 mmol/L to 25 mmol/L, preferably 7.5 mmol/L to 22.5 mmol/L, in particular 8.5 mmol/L to 15.5 mmol/L;

b) Dialkyl carbonate and/or
alkylene carbonate: >5 mmol/L to 25 mmol/L, preferably 7.5 mmol/L to 22.5 mmol/L, in particular 8.5 mmol/L to 15.5 mmol/L.

In this connection, the respective specified concentrations are based on the concentrations of the stated components in the reaction mixture.

The components are preferably reacted at a temperature within the range from 15° C. to 30° C.

The specific size of the calcium carbonate particles can be controlled in a manner known per se via supersaturation.

The calcium carbonate particles precipitate from the reaction mixture under the abovementioned conditions.

The preferably amorphous calcium carbonate particles are expediently stabilized by addition of the preferably surface-active substance to the reaction mixture.

In this connection, said addition of the substance should take place only after the start of the reaction to form the calcium carbonate particles, i.e., only after addition of the reactants, by preference no sooner than 1 minute, preferably no sooner than 2 minutes, expediently no sooner than 3 minutes, particularly preferably no sooner than 4 minutes, in particular no sooner than 5 minutes, after mixing of the reactants. Furthermore, the time of addition should be chosen such that the preferably surface-active substance is added shortly before the end of the precipitation and as shortly as possible before the start of the conversion of the preferably amorphous calcium carbonate into a crystalline form, since the yield and the purity of the "stabilized, sphere-shaped, amorphous calcium carbonate particles" can be maximized in this way. If the addition of the preferably surface-active substance takes place earlier, what is generally obtained is a bimodal product which comprises not only the desired, stabilized, sphere-shaped, amorphous calcium carbonate particles, but also ultrafine, amorphous calcium carbonate particles as secondary product. If the addition of the preferably surface-active substance takes place later, the conversion of the desired "stabilized calcium carbonate particles" into crystalline forms will already start.

For this reason, the preferably surface-active substance is, by preference, added at a pH less than or equal to 11.5, preferably less than or equal to 11.3 and in particular less than or equal to 11.0. What is particularly favorable is an addition at a pH within the range from 11.5 to 10.0, preferably within the range from 11.3 to 10.5 and in particular within the range from 11.0 to 10.8, measured in each case at the reaction temperature, preferably at 25° C.

The resultant, stabilized, preferably sphere-shaped, amorphous calcium carbonate particles can be dewatered and dried in a manner known per se, for example by centrifugation. It is no longer absolutely necessary to wash with acetone and/or to dry in a vacuum drying oven.

By means of drying, "calcium carbonate particles with low structural water content" are obtainable from the "stabilized calcium carbonate particles".

For the purposes of the present invention, the calcium carbonate particles obtained are preferably dried such that they have the desired residual water content. To this end, what has been found to be particularly effective is a procedure in which the calcium carbonate particles are preferably first predried at a temperature up to 150° C. and the calcium carbonate particles are then, by preference, dried at a temperature within the range from greater than 150° C. to 250° C., preferably within the range from 170° C. to 230° C., particularly preferably within the range from 180° C. to 220° C. and in particular within the range from 190° C. to 210° C. The drying preferably takes place in a drying oven with air circulation. In said procedure, the calcium carbonate particles are expediently dried for at least 3 h, particularly preferably for at least 6 h and in particular for at least 20 h.

Within the context of a further particularly preferred embodiment of the present invention, the proportion of crystalline calcium carbonate, in particular of calcitic calcium carbonate, is greater than 10% by weight, preferably greater than 25% by weight, favorably greater than 50% by weight, particularly preferably greater than 70% by weight, very particularly preferably greater than 80% by weight and in particular greater than 90% by weight. Furthermore, the proportion of noncalcitic calcium carbonate forms is preferably less than 50% by weight, particularly preferably less than 30% by weight, very particularly preferably less than 15% by weight and in particular less than 10% by weight. Furthermore, the calcium carbonate particles are as phase-pure as possible. The proportion of peaks of other calcium salts is by preference less than 5%, preferably less than 2% and in particular less than 0.5%. In the best case, peaks of other calcium salt minerals are not detectable by means of X-ray diffraction.

For the ascertainment of the amorphous and the crystalline fractions and of the phase-purity of the material, X-ray diffraction with an internal standard, preferably aluminum oxide, in conjunction with Rietveld refinement has been found to be very particularly effective. The phase-purity is preferably checked by comparison of a measured and a simulated powder diffractogram.

The basicity of the calcium carbonate particles is comparatively low. Their pH, measured in accordance with EN ISO 787-9, is by preference less than 11.5, preferably less than 11.0 and in particular less than 10.5.

The sphere-shaped calcium carbonate particles can be produced by carbonation of an aqueous calcium hydroxide ($Ca(OH)_2$) suspension. To this end, $CO_2$ or a $CO_2$-containing gas mixture is expediently conducted into a calcium hydroxide suspension.

What has been found to be particularly effective is a procedure in which a. an aqueous calcium hydroxide suspension is initially charged, b. carbon dioxide or a carbon dioxide-containing gas mixture is introduced into the suspension from step a. and c. the resultant calcium carbonate particles are separated off, with 0.3% by weight to 0.7% by weight, preferably 0.4% by weight to 0.6% by weight and in particular 0.45% by weight to 0.55% by weight of at least one aminotrisalkylenephosphonic acid being further added.

The concentration of the calcium hydroxide suspension is not subject to any particular restrictions. However, a concentration within the range from 1 g CaO/L to 100 g CaO/L, preferably within the range from 10 g CaO/L to 90 g CaO/L and in particular within the range from 50 g CaO/L to 80 g CaO/L is particularly favorable.

The aminotrisalkylenephosphonic acid added is preferably aminotrismethylenephosphonic acid, aminotrisethylenephosphonic acid, aminotrispropylenephosphonic acid and/or aminotrisbutylenephosphonic acid, in particular aminotrismethylenephosphonic acid.

It is possible to control the conversion of the reaction via the amount of $CO_2$ introduced. However, the carbon dioxide or the carbon dioxide-containing gas mixture is preferably introduced until the reaction mixture has a pH less than 9, preferably less than 8 and in particular less than 7.5.

Furthermore, the carbon dioxide or the carbon dioxide-containing gas mixture is expediently introduced into the calcium hydroxide suspension at a gas flow rate within the range from 0.02 L $CO_2$/(h*g $Ca(OH)_2$) to 2.0 L $CO_2$/(h*g $Ca(OH)_2$), preferably within the range from 0.04 L $CO_2$/(h*g $Ca(OH)_2$) to 1.0 L $CO_2$/(h*g $Ca(OH)_2$), particularly preferably within the range from 0.08 L $CO_2$/(h*g $Ca(OH)_2$) to 0.4 L $CO_2$/(h*g $Ca(OH)_2$) and in particular within the range from 0.12 L $CO_2$/(h*g $Ca(OH)_2$) to 0.2 L $CO_2$/(h*g $Ca(OH)_2$).

Apart from that, the conversion of the calcium hydroxide suspension with the carbon dioxide or the carbon dioxide-containing gas mixture takes place by preference at a temperature less than 25° C., preferably less than 20° C. and in particular less than 15° C. On the other hand, the reaction temperature is by preference greater than 0° C., preferably greater than 5° C. and in particular greater than 7° C.

The addition of the at least one aminotrisalkylenephosphonic acid expediently takes place during the course of the reaction, preferably after an abrupt drop in the conductance of the reaction mixture. Expediently, the at least one aminotrisalkylenephosphonic acid is added once the conductivity of the reaction mixture falls by more than 0.5 mS/cm/min. In this connection, the decrease in the conductance of the reaction mixture is preferably at least 0.25 mS/cm within 30 seconds, in particular at least 0.5 mS/cm within 60 seconds. Within the context of a particularly preferred embodiment of the present invention, the addition of the at least one aminotrisalkylenephosphonic acid takes place at the end of the precipitation of the basic calcium carbonate (BCC; $2CaCO_3*Ca(OH)_2*nH_2O$).

The calcium carbonate particles precipitate from the reaction mixture under the abovementioned conditions and can be separated off and dried in a manner known per se.

Within the context of a preferred embodiment of the present invention, the composite powder according to the invention contains in addition to calcium carbonate also other calcium salts, preferably calcium phosphates, especially $Ca_3(PO_4)_2$, $CaHPO_4$, $Ca(H_2PO_4)_2$ and/or $Ca_5(PO_4)_3$(OH). In this connection, the weight ratio of calcium carbonate to calcium phosphate is preferably within the range from 99:1 to 1:99 and in particular within the range from 50:50 to 99:1.

Within the context of a preferred embodiment of the present invention, the small particles comprise inhibitory calcium carbonate particles. In this context, "inhibitory calcium carbonate particles" refer to calcium carbonate particles which, as additive in polymers, slow down, in the best case, completely suppress the acid-catalyzed degradation of the polymer in comparison with the same polymer without additive.

Expediently, the small particles are obtainable by means of a method in which calcium carbonate particles are coated with a composition comprising, based on its total weight, at least 0.1% by weight of at least one weak acid.

Within the context of a particularly preferred embodiment of the present invention, the inhibitory calcium carbonate is obtainable by means of a method in which calcium carbonate particles are coated with a composition comprising, based in each case on its total weight, a mixture of at least 0.1% by weight of at least one calcium complexing agent and/or at least one conjugate base, which is an alkali-metal or calcium salt of a weak acid, together with at least 0.1% by weight of at least one weak acid.

Within the context of this embodiment, the anions of the calcium complexing agent and of the conjugate base can be the same, though this is not absolutely necessary.

Sodium phosphates, i.e., sodium salts of phosphoric acids, especially sodium salts of orthophosphoric acid, metaphosphoric acid and polyphosphoric acid, have been found to be very particularly advantageous as calcium complexing agents. Preferred sodium phosphates encompass sodium orthophosphates, such as primary sodium dihydrogenphosphate $NaH_2PO_4$, secondary sodium dihydrogenphosphate $Na_2HPO_4$ and tertiary trisodium phosphate $Na_3PO_4$; sodium isopolyphosphates, such as tetrasodium diphosphate (sodium pyrophosphate) $Na_4P_2O_7$, pentasodium triphosphate (sodium tripolyphosphate) $Na_5P_3O_{10}$; and higher-molecular-weight sodium phosphates, such as sodium metaphosphates and sodium polyphosphates, such as fused or calcined phosphates, Graham's salt (approximate composition $Na_2O*P_2O_5$, sometimes also referred to as sodium hexametaphosphate), Kurrol's salt and Maddrell's salt. According to the invention, very particular preference is given to using sodium hexametaphosphate. The use of the abovementioned phosphates is particularly advantageous especially in a composite powder for implants, since the phosphates additionally promote bone formation in this case.

Further suitable calcium complexing agents include joint polydentate, chelating ligands, especially ethylenediaminetetraacetic acid (EDTA), triethylenetetramine, diethylenetriamine, o-phenanthroline, oxalic acid and mixtures thereof.

Weak acids particularly suitable for the purposes of the present invention have a $pK_a$, measured at 25° C., greater than 1.0, preferably greater than 1.5 and in particular greater than 2.0. At the same time, the $pK_a$ of suitable weak acids, measured at 25° C., is by preference less than 20.0, preferably less than 10.0, particularly preferably less than 5.0, expediently less than 4.0 and in particular less than 3.0. Weak acids very particularly suitable according to the invention encompass phosphoric acid, metaphosphoric acid, hexametaphosphoric acid, citric acid, boric acid, sulfurous acid, acetic acid and mixtures thereof. Phosphoric acid is very particularly preferably used as weak acid.

Conjugate bases preferred according to the invention include especially sodium or calcium salts of the abovementioned weak acids, with very particular preference being given to sodium hexametaphosphate.

The inhibitory calcium carbonate particles can be produced in a manner known per se by coating calcium carbonate particles with a composition comprising at least one weak acid.

Particularly preferably, the inhibitory calcium carbonate particles are produced in a manner known per se by coating calcium carbonate particles with a composition comprising at least one calcium complexing agent and/or at least one conjugate base, which is an alkali-metal or calcium salt of a weak acid, together with at least one weak acid. The simultaneous coating with at least one calcium complexing agent and/or at least one conjugate base, which is an alkali-metal or calcium salt of a weak acid, together with at least one weak acid leads to particularly preferred calcium carbonate particles.

Expediently, what is initially charged is an aqueous suspension of the calcium carbonate particles to be coated, which, based on its total weight, favorably has a content of calcium carbonate particles within the range from 1.0% by weight to 80.0% by weight, preferably within the range from 5.0% by weight to 50.0% by weight and in particular within the range from 10.0% by weight to 25.0% by weight.

The calcium carbonate particles are favorably coated by addition of the stated substance or substances in pure form or in aqueous solution, with aqueous solutions of the stated component or components having been found to be very particularly advantageous according to the invention for achieving a coating of the calcium carbonate particles which is as homogeneous as possible.

Furthermore, it is particularly favorable within the context of the present invention to add the calcium complexing agent and/or the conjugate base, which is an alkali-metal or calcium salt of a weak acid, before the weak acid.

The calcium complexing agent or the conjugate base is used by preference in an amount within the range from 0.1 part by weight to 25.0 parts by weight, preferably within the range from 0.5 part by weight to 10.0 parts by weight and in particular within the range from 1.0 part by weight to 5.0 parts by weight, based in each case on 100 parts by weight of the calcium carbonate particles to be coated. In this connection, the amount of the calcium complexing agent or of the conjugate base is expediently chosen such that a complete coating of the surface of the calcium carbonate particles with the calcium complexing agent the conjugate base is achieved.

The weak acid is used by preference in an amount within the range from 0.1 part by weight to 30.0 parts by weight, preferably within the range from 0.5 part by weight to 15.0 parts by weight, particularly preferably within the range from 1.0 part by weight to 10.0 parts by weight and in particular within the range from 4.0 parts by weight to 8.0 parts by weight, based in each case on 100 parts by weight of the calcium carbonate particles to be coated.

The inhibitory calcium carbonate particles obtainable in this way are stable in a moderately acidic environment, this capability being attributed to a buffer effect due to the weak acid, preferably due to the absorbed or reacted calcium complexing agent or the conjugate base on the surface of the calcium carbonate particles and the weak acid, with especially the application of the calcium complexing agent and/or of the conjugate base on the surface of the calcium carbonate particles lowering in turn the solubility of the surface of the calcium carbonate particles and thus stabilizing the calcium carbonate particles, without it being intended that the teaching of the present invention be tied to this theory.

The composite powder is, according to the invention, obtainable by means of a method in which large particles are combined with small particles, wherein the large particles have an average particle diameter within the range from 0.1 μm to 10 mm, preferably within the range from 5 μm to 10 mm, particularly preferably within the range from 10 μm to 10 mm, favorably within the range from 20 μm to 10 mm, advantageously within the range from 30 μm to 2.0 mm and in particular within the range from 60.0 μm to 500.0 μm, the average particle diameter of the small particles is by preference not more than $\frac{1}{5}$, preferably not more than $\frac{1}{10}$, particularly preferably not more than $\frac{1}{20}$ and in particular not more than $\frac{1}{1000}$ of the average particle diameter of the large particles.

In this connection, the small particles are arranged on the surface of the large particles and/or distributed inhomogeneously within the large particles. Within the context of a particularly preferred embodiment of the present invention, especially for resorbable polymers and for UHMWPE, excellent results are achieved, however, when the small particles are arranged at least in part on the surface of the large particles and preferably cover them incompletely. Very particularly preferably, the small particles are arranged on the surface of the large particles and preferably cover them incompletely.

Here, an "inhomogeneous" distribution of the small particles or fragments thereof within the large particles means a distribution of the small particles or fragments thereof within the large particles that is not homogeneous (uniform). Preferably, there are, within the particles of the composite powder, at least one first region that comprises at least two, by preference at least three, preferably at least four and in particular at least five small particles or fragments thereof and at least one other region within the particles of the composite powder that has the same volume and the same shape as the first region, but comprises a different number of small particles.

Within the context of a preferred embodiment of the present invention, the weight ratio of polymer, especially polyamide, to precipitated calcium carbonate in the particle interior is greater than the weight ratio of polymer, especially polyamide, to precipitated calcium carbonate in the exterior of the particles. Expediently, the weight ratio of polymer, especially polyamide, to precipitated calcium carbonate in the particle interior is greater than 50:50, preferably greater than 60:40, favorably greater than 70:30, particularly preferably greater than 80:20, yet more preferably greater than 90:10, very particularly preferably greater than 95:5 and in particular greater than 99:1. Furthermore, the weight ratio of precipitated calcium carbonate to polymer, especially polyamide, in the exterior of the particles, preferably in the preferential exterior of the particles, is greater than 50:50, preferably greater than 60:40, favorably greater than 70:30, particularly preferably greater than 80:20, yet more preferably greater than 90:10, very particularly preferably greater than 95:5 and in particular greater than 99:1.

Within the context of a further preferred embodiment of the present invention, the small particles are arranged on the surface of the large particles and preferably cover the large particles incompletely. Expediently, at least 0.1%, preferably at least 5.0% and in particular 50.0% of the surface of the large particles are not coated with the sphere-shaped calcium carbonate particles. Preferably, this effect is enhanced by the gaps between individual calcium carbonate particles, which are preferably present and lead to the formation of corresponding microchannels for fluidic substances, especially for a polymer melt of the large particles. This structure is especially advantageous for uses of the composite powder in laser sintering methods, since this ensures a uniform and rapid melting of the polymer present in the composite powder, preferably the thermoplastic polymer, particularly preferably the resorbable polymer, in particular the lactic acid polymer.

Within the context of a particularly preferred embodiment of the present invention, the composite powder according to the invention is characterized by a specific particle-size distribution. Firstly, the particles of the composite powder have, by preference, an average particle size $d_{50}$ within the range from 10 µm to less than 200 µm, preferably within the range from 20 µm to less than 200 µm, particularly preferably within the range from 20 µm to less than 150 µm, favorably within the range from 20 µm to less than 100 µm and in particular within the range from 35 µm to less than 70 µm.

Furthermore, fine-particle proportion of the composite powder is by preference less than 50.0% by volume, preferably less than 45.0% by volume, particularly preferably less than 40.0% by volume, yet more preferably less than 20.0% by volume, favorably less than 15.0% by volume, expediently less than 10.0% by volume and in particular less than 5.0% by volume. In this connection, the fine-particle proportion refers to, according to the invention, the proportion of the smallest particle population in the case of a bimodal or multimodal particle-size distribution, based on the total amount for the cumulative distribution curve. In the case of a unimodal (monodisperse) particle-size distribution, the fine-particle proportion is, according to the invention, defined as 0.0% by volume. In this context, what are taken into consideration are all particles present in the product, including noncombined starting material, especially small particles within the context of the invention as well as fragments of the large and/or the small particles within the context of the invention.

For composite powder having an average particle size $d_{50}$ within the range from greater than 40 µm to less than 200 µm, the fine-particle proportion is preferably such that the proportion of particles in the product having a particle size less than 20 µm is by preference less than 50.0% by volume, preferably less than 45.0% by volume, particularly preferably less than 40.0% by volume, yet more preferably less than 20.0% by volume, favorably less than 15.0% by volume, expediently less than 10.0% by volume and in particular less than 5.0% by volume, with "particles" in this context encompassing especially particles of the composite powder within the context of the invention, small particles within the context of the invention and fragments of the large and/or the small particles within the context of the invention, provided that they have the stated particle size.

For composite powder having an average particle size $d_{50}$ within the range from 10 µm to 40 µm, the fine-particle proportion is preferably such that the proportion of particles in the product having a particle size less than 5 µm is by preference less than 50.0% by volume, preferably less than 45.0% by volume, particularly preferably less than 40.0% by volume, yet more preferably less than 20.0% by volume, favorably less than 15.0% by volume, expediently less than 10.0% by volume and in particular less than 5.0% by volume, with "particles" in this context encompassing especially particles of the composite powder within the context of the invention, small particles within the context of the invention and fragments of the large and/or the small particles within the context of the invention, provided that they have the stated particle size.

Furthermore, the density of the fine-particle proportion is by preference less than 2.6 g/cm$^3$, preferably less than 2.5 g/cm$^3$, particularly preferably less than 2.4 g/cm$^3$ and in particular within the range from greater than 1.2 g/cm$^3$ to less than 2.4 g/cm$^3$, with this value preferably being determined by separating off the fine-particle proportion by means of sieving and by measuring the density of the fraction separated off.

Preferably, the particles of the composite powder have a particle size $d_{90}$ of less than 350 µm, by preference less than 300 µm, preferably less than 250 µm, particularly preferably less than 200 µm and in particular less than 150 µm.

Furthermore, the particle size $d_{90}$ is by preference greater than 50 µm, preferably greater than 75 µm and in particular greater than 100 µm.

Expediently, the ratio $d_{20}/d_{50}$ is less than 100%, by preference less than 75%, preferably less than 65%, particularly preferably less than 60% and in particular less than 55%. Furthermore, the ratio $d_{20}/d_{50}$ is expediently greater than 10%, by preference greater than 20%, preferably greater than 30%, particularly preferably greater than 40% and in particular greater than 50%.

Within the context of the present invention, the above-mentioned variables $d_{20}$, $d_{50}$ and $d_{90}$ are defined as follows:

$d_{20}$ refers to the particle size of the particle-size distribution, at which 20% of the particles have a particle size less than the specified value and 80% of the particles have a particle size greater than or equal to the specified value.

$d_{50}$ refers to the average particle size of the particle-size distribution. 50% of the particles have a particle size less than the specified value and 50% of the particles have a particle size greater than or equal to the specified value.

$d_{90}$ refers to the particle size of the particle-size distribution, at which 90% of the particles have a particle size less than the specified value and 10% of the particles have a particle size greater than or equal to the specified value.

The particle-size distribution of this embodiment can be achieved in a manner known per se by classification of the composite powder, i.e., by separation of a disperse solids mixture into fractions. Preferably, classification is done according to particle size or particle density. Dry sieving, wet sieving and air-jet sieving, especially air-jet sieving, as well as flow classification, especially by means of air classification, are particularly advantageous.

Within the context of a particularly preferred embodiment of the present invention, the composite powder is classified in a first step for maximum removal of the coarse fraction greater than 800 µm, preferably greater than 500 µm and in particular greater than 250 µm. In this context, what has been found to be particularly effective is dry sieving over a coarse sieve which has, by preference, a size within the range from 250 µm to 800 µm, preferably within the range from 250 µm to 500 µm and in particular of 250 µm, with size meaning the size of the openings.

In a further step, the composite powder is preferably classified for maximal removal of the fine fraction<20 µm. In this context, air-jet sieving and air classification have been found to be particularly favorable.

According to the invention, the average diameter of the particles of the composite powder, of the large particles and of the small particles, the particle sizes $d_{20}$, $d_{50}$, $d_{90}$ and also the abovementioned longitudinal sizes are expediently ascertained on the basis of micrographs, possibly on the basis of electron micrographs. For the ascertainment of the average diameter of the large particles and of the small particles and also of the particles of the composite powder and for the particle sizes $d_{20}$, $d_{50}$, $d_{90}$, sedimentation analyses are also particularly advantageous, with the use of a Sedigraph 5100 (Micromeritics GmbH) being particularly favorable here. For the particles of the composite powder, particle-size analyses with laser diffraction have also been found to be particularly effective, with the use of a HELOS/F laser diffraction sensor from Sympatec GmbH being particularly advantageous in this context. It preferably comprises a RODOS dry disperser.

Apart from that, these data and also all other data in the present description are, unless otherwise specified, based on a temperature of 23° C.

The composite powder according to the invention is comparatively compact. By preference, the proportion of subregions inside the particles of the composite powder that have a density less than 0.5 g/cm$^3$ and in particular less than 0.25 g/cm$^3$ is less than 10.0%, preferably less than 5.0% and in particular less than 1.0%, based in each case on the total volume of the composite powder.

The proportion by weight of the sphere-shaped calcium carbonate particles, based on the total weight of the composite powder, is by preference at least 0.1% by weight, preferably at least 1.0% by weight and particularly preferably at least 5.0% by weight and is expediently within the range from 5.0% by weight to 80.0% by weight, particularly preferably within the range from 10.0% by weight to 60.0% by weight and favorably within the range from 20.0% by weight to 50.0% by weight. For sphere-shaped calcium carbonate particles, which, based on the total amount of sphere-shaped calcium carbonate particles, contain more than 15.0% by weight of particles of a size less than 20 µm and/or particles of a size greater than 250 µm, what has been found to be very particularly effective is a total amount of sphere-shaped calcium carbonate particles within the range from 35.0% by weight to 45.0% by weight. For sphere-shaped calcium carbonate particles, which, based on the total amount of sphere-shaped calcium carbonate particles, contain not more than 15.0% by weight of particles of a size less than 20 µm and/or particles of a size greater than 250 µm, what has been found to be very particularly effective is a total amount of sphere-shaped calcium carbonate particles within the range from 20.0% by weight to 30.0% by weight.

The proportion by weight of the polymer and preferably of the thermoplastic polymer, based on the total weight of the composite powder, is by preference at least 0.1% by weight, preferably at least 1.0% by weight and particularly preferably at least 5.0% by weight and is expediently within the range from 20.0% by weight to 95.0% by weight, preferably within the range from 40.0% by weight to 90.0% by weight and favorably within the range from 50.0% by weight to 80.0% by weight.

For a composite powder containing sphere-shaped calcium carbonate particles, which, based on the total amount of sphere-shaped calcium carbonate particles, contain more than 20.0% by weight of particles of a size less than 20 µm and/or particles of a size greater than 250 µm, what has been found to be very particularly effective is a total amount of polymer within the range from 55.0% by weight to 65.0% by weight. For a composite powder containing sphere-shaped calcium carbonate particles, which, based on the total amount of sphere-shaped calcium carbonate particles, contain not more than 20.0% by weight of particles of a size less than 20 µm and/or particles of a size greater than 250 µm, what has been found to be very particularly effective is a total amount of polymer within the range from 70.0% by weight to 80.0% by weight.

The composite powder is distinguished by, inter alia, a very good combination of the first material with the second material. The firm combination of the first material with the second material can preferably be verified by subjecting the composite powder to mechanical stress, especially by shake extraction of the composite powder with nonsolvent for the polymer and sphere-shaped calcium carbonate at 25° C., preferably in accordance with the procedure described in *Organikum*, 17th edition, VEB Deutscher Verlag der Wissenschaften, Berlin, 1988, section 2.5.2.1 *"Ausschütteln von Lösungen bzw. Suspensionen"* [shake extraction of solutions or suspensions], pages 56-57. The shake time is by preference at least one minute, preferably at least 5 minutes and in particular 10 minutes, and preferably does not lead to a substantial change in the shape, the size and/or the composition of the particles of the composite powder. Particularly preferably, there is no change after the shake test for at least 60% by weight, by preference at least 70% by weight, preferably at least 80% by weight, particularly preferably at least 90% by weight, favorably at least 95% by weight and in particular at least 99% by weight of the particles of the composite powder, with respect to their composition, their size and preferably their shape. A nonsolvent which is particularly suitable in this context is water, especially for polyamide-containing composite powder.

Furthermore, the particles of the composite powder according to the invention usually have a comparatively isotropic particle shape, which is especially advantageous for uses of the composite powder in SLM methods. The normally virtually sphere-shaped particle shape of the particles of the composite powder generally leads to an avoidance or at least to a reduction of negative influences, such as warpage or shrinkage. Consequently, a very advantageous melting and solidification behavior of the composite powder can usually also be observed.

In contrast, conventional powder particles, which are obtained by cryogenic grinding for example, have an irregular (amorphous) particle shape with sharp edges and pointed corners. However, such powders are not advantageous for SLM methods because of their disadvantageous particle shape and additionally because of their comparatively wide particle-size distribution and because of their comparatively high fine fraction of particles<20 µm.

By means of the calcium carbonate particles and especially by means of the precipitated calcium carbonate particles, it is possible to specifically influence and control the properties of the polymer, especially of the thermoplastic polymer. For instance, the calcium carbonate particles and especially the precipitated calcium carbonate particles allow a very good buffering and pH stabilization of the polymer, especially of the thermoplastic polymer. Furthermore, the biocompatibility of the polymer, especially of the thermoplastic polymer, is distinctly improved by the calcium carbonate particles and especially by the precipitated calcium carbonate particles. Furthermore, a distinct suppression of the thermal degradation of the polymer, especially of the thermoplastic polymer, is observed when using the inhibitory calcium carbonate particles.

The composite powder according to the invention can be produced in a manner known per se, for example by means of a one-step method, especially by surface precipitation or coating, preferably by coating with grinding material. Furthermore, what is also particularly suitable is a procedure in which polymer particles are precipitated from a polymer solution which additionally contains small particles within the context of the invention, preferably in suspended form.

However, what has been found to be particularly effective is a procedure in which polymer particles and sphere-shaped calcium carbonate particles are contacted with one another and are combined with one another by the action of mechanical forces. Expediently, this is done in a suitable mixer or in a mill, especially in an impact mill, pin mill or in an ultrarotor mill. In this connection, the rotor speed is by preference greater than 1 m/s, preferably greater than 10 m/s, particularly preferably greater than 25 m/s and in particular within the range from 50 m/s to 100 m/s.

The temperature at which the composite powder is produced can fundamentally be freely chosen. However, temperatures greater than −200° C., by preference greater than −100° C., preferably greater than −50° C., particularly preferably greater than −20° C. and in particular greater than 0° C. are particularly advantageous. On the other hand, the temperature is advantageously less than 120° C., by preference less than 100° C., preferably less than 70° C., particularly preferably less than 50° C. and in particular less than 40° C. Temperatures within the range from greater than 0° C. to less than 50° C. and in particular within the range from greater than 5° C. to less than 40° C. have been found to be very particularly effective.

Within the context of a particularly preferred embodiment of the present invention, the mixer or the mill, especially the impact mill, the pin mill or the ultrarotor mill, is cooled during the production of the composite powder according to the invention in order to dissipate the energy which is released. By preference, cooling is achieved with a coolant having a temperature less than 25° C., preferably within the range from less than 25° C. to −60° C., particularly preferably within the range from less than 20° C. to −40° C., expediently within the range from less than 20° C. to −20° C. and in particular within the range from less than 15° C. to 0° C. Furthermore, the cooling is preferably dimensioned such that, at the end of the mixing or grinding operation, preferably the grinding operation, the temperature in the mixing or grinding space, preferably in the grinding space, is less than 120° C., by preference less than 100° C., preferably less than 70° C. particularly preferably less than 50° C. and in particular less than 40° C.

According to a particularly preferred embodiment of the present invention, this procedure leads, especially in the case of polyamides, to the sphere-shaped calcium carbonate particles penetrating into the interior of the polymer particles and being covered by the polymer as completely as possible, with the result that they are not identifiable from the outside. Such particles can be processed and used like the polymer without the sphere-shaped calcium carbonate particles, but have the improved properties of the composite powder according to the invention.

Within the context of a first particularly preferred variant of the present invention, the composite powder is produced following the procedure described in the patent application JP62083029 A. In this procedure, a first material (so-called mother particles) is coated on the surface with a second material consisting of smaller particles (so-called baby particles). For this purpose, preference is given to using a surface-modification device ("hybridizer") which comprises a high-speed rotor, a stator and a sphere-shaped vessel, preferably comprising internal blades. The use of NARA hybridization systems, which preferably have an outer rotor diameter of 118 mm, especially of a hybridization system with the designation NHS-0 or NHS-1 from NARA Machinery Co., Ltd., has been found to be particularly effective in this context.

The mother particles and the baby particles are mixed, preferably finely distributed and introduced into the hybridizer. There the mixture is preferably further finely distributed and preferably repeatedly exposed to mechanical forces, especially impact forces, compression forces, friction forces and shear forces as well as the mutual interactions of the particles, in order to embed the baby particles in the mother particles in a uniform manner.

Preferred rotor speeds are within the range from 50 m/s to 100 m/s, based on the circumferential speed.

For further details in relation to this method, especially with regard to the particularly expedient embodiments, reference is made to JP62083029 A, the disclosure of which, including the particularly expedient method variants, is explicitly incorporated into the present application by reference.

Within the context of a further particularly preferred variant of the present invention, the composite powder is produced following the procedure described in the patent application DE 42 44 254 A1. Accordingly, a method for producing a composite powder by attaching a substance on the surface of a thermoplastic material is particularly favorable when the thermoplastic material has an average particle diameter of from 100 μm to 10 mm and the substance has a smaller particle diameter and a better heat resistance than the thermoplastic material, especially when the method comprises the steps of:

first heating the substance which has the smaller particle diameter and the better heat resistance than the thermoplastic material to a temperature which is preferably not less than the softening point of the thermoplastic material, while stirring in a device which preferably has a stirrer and a heater;

adding the thermoplastic material into the device; and attaching the substance having the better heat resistance on the surface of the thermoplastic material.

For further details in relation to this method, especially with regard to the particularly expedient embodiments, reference is made to DE 42 44 254 A1, the disclosure of which, including the particularly expedient method variants, is explicitly incorporated into the present application by reference.

Within the context of yet a further particularly preferred variant of the present invention, the composite powder is produced following the procedure described in the patent application EP 0 922 488 A1 and/or in the U.S. Pat. No. 6,403,219 B1. Accordingly, what is particularly advantageous is a method for producing a composite powder by attaching or adhesively mounting fine particles on the surface of a solid particle which acts as a core, by application of an impact and subsequent growth of one or more crystals on the core surface.

For further details in relation to this method, especially with regard to the particularly expedient embodiments, reference is made to the patent application EP 0 922 488 A1 and/or the U.S. Pat. No. 6,403,219 B1, the disclosures of which, including the particularly expedient method variants, are explicitly incorporated into the present application by reference.

Within the context of a further particularly preferred embodiment of the present invention, the composite powder is subjected to a fixing operation following the procedure described in the patent application EP 0 523 372 A1. This procedure is especially expedient for a composite powder which were obtained following the method described in the patent application JP62083029 A. In this connection, the particles of the composite powder are preferably fixed by means of thermal plasma spraying, with preference being given to using a reduced-pressure plasma spraying device which preferably has an output of at least 30 kW, especially the instrument described in EP 0 523 372 A1.

For further details in relation to this method, especially with regard to the particularly expedient embodiments, reference is made to the patent application EP 0 523 372 A1, the disclosure of which, including the particularly expedient method variants, is explicitly incorporated into the present application by reference.

The composite powder according to the invention is distinguished by an excellent property profile which suggests its use especially in laser sintering methods. Its excellent pourability and its excellent flowability allow, in the case of laser sintering, the production of components having excellent surface quality and surface nature as well as improved component density. At the same time, the composite powder according to the invention exhibits a very good shrinkage behavior and an excellent dimensional stability. Furthermore, a better heat-conductivity behavior outside the laser-treated region can be established.

Furthermore, the composite powder according to the invention has a comparatively high isotropy, which allows an extremely uniform melting of the composite powder. This behavior can be utilized in SLM methods for the production of components having high quality, high component density, low porosity and low number of imperfections.

Furthermore, the presence of the sphere-shaped calcium carbonate particles in the composite powder allows an excellent pH stabilization (buffering) in later applications, especially in those polymers which contain acid groups or can release acids under certain conditions. These include, for example, polyvinyl chloride and polylactic acid.

Furthermore, any other, more expensive materials can be replaced with the composite powder according to the invention in order to thus achieve a price reduction of the end product.

According to the invention, the properties of the composite powder, especially its flowability, can also be controlled and, if needed, specifically adjusted via the moistness of the composite powder. On the one hand, the flowability of the composite powder fundamentally increases with increasing moistness, which facilitates the processability of the composite powder. On the other hand, a higher moistness of the composite powder can, especially in the case of thermal processing of the composite powder, particularly in the presence of impurities and/or the presence of very fine particles, lead to thermal degradation or hydrolysis of the polymer and to process disturbances.

Against this background, the moistness of the composite powder according to the invention is by preference less than 2.5% by weight, preferably less than 1.5% by weight, particularly preferably less than 1.0% by weight, yet more preferably less than 0.9% by weight, favorably less than 0.8% by weight, expediently less than 0.6% by weight, very particularly preferably less than 0.5% by weight and in particular less than 0.25% by weight. On the other hand, the moistness of the composite powder according to the invention is by preference greater than 0.000% by weight, preferably greater than 0.010% by weight and in particular greater than 0.025% by weight.

In this context, the use of the inhibitory calcium carbonate allows an again improved thermal processability of the composition. The processing window (temperature window) is distinctly greater than with conventional calcium carbonate and a thermal degradation or a hydrolysis of a polymer is again significantly suppressed.

The desired moistness of the composite powder can be achieved by inherently known predrying of the composite powder prior to processing, with drying in the production process being fundamentally advisable. For a stable process management, what has been found to be very particularly favorable in this context is drying up to a moisture content within the range from 0.01% by weight to 0.1% by weight. Furthermore, the use of a microwave vacuum dryer has been found to very particularly effective.

The further processing of the composite powder can be done comparatively easily, since, according to the solution according to the invention, only one component (the composite powder) and no longer two components (sphere-shaped calcium carbonate particles and polymer) are to be processed. Dispersion problems are not noticeable owing to the firm combination between the polymer and the sphere-shaped calcium carbonate particles.

Furthermore, it is possible, via the choice of the proportions and of the size of the particular individual components, to specifically control the microstructure, the melting behavior and the flow behavior of the composite powder. These properties of the composite powder can in turn be utilized in order to specifically control the end structure of the resultant components, especially their biological compatibility, their biodegradability and their mechanical properties.

It is generally not necessary to add further processing aids, especially specific solvents, when processing the composite powder. This extends the possible application areas of the composite powder especially in the pharmaceutical sector and in the food sector.

The composite powder can be directly used as such. Owing to its excellent property profile, the composite powder is, however, especially suitable as additive, particularly preferably as polymer additive, as additive substance or starting material for compounding, for the production of components, for applications in medical technology and/or in microtechnology and/or for the production of foamed articles. Particularly preferred medical technology applications preferably include resorbable implants. Particularly expedient application areas encompass injection-molded screws, pressed plates, especially melt-pressed plates, foamed implants and pourable powders for selective manufacturing methods, and, in the last case, the overall particle size of the particles of the composite powder is preferably less than 3 mm and preferably greater than 5.0 µm.

As polymer additive, the composite powder is preferably added to at least one polymer, especially one thermoplastic polymer, as matrix polymer. Here, particular preference is given to the polymers which can also be used as component of the composite powder. To avoid repetition, reference is therefore made to the above remarks, especially with respect to the preferred forms of the polymer. Very particularly preferred matrix polymers include polyvinyl chloride (PVC), polyurethane (PU), silicone, polypropylene (PP), polyethylene (PE), especially UHMWPE, and polylactic acid (PLA).

Within the context of the present invention, the matrix polymer and the polymer of the composite powder are preferably miscible with one another at the application temperature, particularly preferably chemically identical.

Particularly preferred compositions contain 40.0% by weight to 99.9% by weight of at least one matrix polymer and 0.1% by weight to 50.0% by weight of at least one composite powder according to the invention.

The composition can be produced in a manner known per se by mixing the components.

The composition can then be further processed in a customary manner, in particular granulated, ground, extruded, injection-molded, foamed or else used in 3D-printing methods.

Furthermore, the composite powder can be further processed and/or used directly, i.e., without addition of additional polymers.

The advantages of the composite powder are, in this connection, noticeable especially when granulating, grinding, extruding, injection-molding, melt-pressing, foaming and/or 3D-printing the composite powder.

Within the context of the present invention, polymer foams are preferably produced by the generation or introduction of a gaseous phase into a composition comprising the composite powder and possibly at least one matrix polymer. In this case, the goal is to distribute the gas in the composition as uniformly as possible in order to achieve a uniform and homogeneous foam structure. The gas can be introduced in different ways.

Preferably, the gas phase is generated by addition of a blowing agent. Blowing agents refer to substances which release gases as a result of chemical reactions (chemical blowing agents) or as a result of phase transition (physical blowing agents). In the case of foam extrusion or in the case of foam injection-molding, the chemical blowing agent is admixed in the mold of a master batch of the composition or physical blowing agent is directly injected under pressure into the melt of the composition. The injection is referred to as direct gas-injection and is used especially when processing thermoplastic polymers.

Furthermore, the composite powder according to the invention is especially suitable for the production of implants which can replace conventional metal implants for bone fractures. The implants serve to fix the bones until the fracture is healed. Whereas metal implants normally remain in the body or must be removed in a further operation, the implants obtainable from the composite powder according to the invention act as a temporary aid. They expediently comprise polymers which the body itself can degrade and substances which supply calcium and preferably valuable phosphorus substances for bone formation. The advantages which arise for the patient are clear: no further operation for the removal of the implant and a quickened bone regeneration.

According to a particularly preferred variant of the present invention, the composite powder according to the invention is used for the production of components, especially implants, by means of selective laser sintering. Expediently, a bed of powder of tightly packed particles of the composite powder according to the invention is easily partially or fully melted locally (just the polymer) with the aid of a laser scanner unit, a directly deflected electron beam or an infrared heater with a geometry-representing mask. The particles solidify owing to cooling as a result of heat transfer and thus combine to form a solid layer. The powder particles which are not partially melted remain as support material in the component and are preferably removed after the construction process has ended. By means of renewed coating with powder, it is possible, in analogy with the first layer, for further layers to be hardened and to be combined with the first layer.

Laser types particularly suitable for laser sintering methods are all the ones which cause the polymer of the composite powder according to the invention to sinter, to fuse or to crosslink, in particular CO2 laser (10 μm) ND-YAG laser (1060 nm), He—Ne laser (633 nm) or dye laser (350-1000 nm). Preference is given to using a CO2 laser.

In the case of the irradiation, the energy density in the packed bed is, by preference, from 0.1 $J/mm^3$ to 10 $J/mm^3$.

Depending on the application, the effective diameter of the laser beam is, by preference, from 0.01 nm to 0.5 nm, preferably 0.1 nm to 0.5 nm.

Preference is given to using pulsed lasers, with a high pulse frequency, especially from 1 kHz to 100 kHz, having been found to be particularly suitable.

The preferred procedure can be described as follows: The laser beam strikes the top layer of the packed bed composed of the material to be used according to the invention and, while doing so, sinters the material within a certain layer thickness. Said layer thickness can be from 0.01 mm to 1 mm, preferably from 0.05 mm to 0.5 mm. The first layer of the desired component is generated in this way. Thereafter, the working space is lowered by an amount which is lower than the thickness of the layer sintered together. The working space is filled up to the original level with additional polymer material. By means of renewed irradiation with the laser, the second layer of the component is sintered and combined with the previous layer. By repeating the operation, the further layers are generated until the component is completed.

The exposure rate in the case of the scanning of the laser is preferably 1 mm/s to 1000 mm/s. Typically, a rate of about 100 mm/s is used.

In the present case, what has been found to be particularly effective for the partial or full melting of the polymer is heating to a temperature within the range from 60° C. to 250° C., preferably within the range from 100° C. to 230° C. and in particular within the range from 150° C. to 200° C.

The present invention also provides components obtainable by selective laser sintering of a composition comprising a composite powder according to the invention, with implants for uses in the field of neurosurgery, oral surgery, jaw surgery, facial surgery, neck surgery, nose surgery and ear surgery as well as hand surgery, foot surgery, thorax surgery, rib surgery and shoulder surgery being excluded as components.

The proportion by weight of the composite powder according to the invention in the composition is by preference at least 50.0% by weight, preferably at least 75.0% by weight, particularly preferably at least 90.0% by weight and in particular at least 99.0% by weight. Within the context of a very particularly embodiment of the present invention, the composition contains only the composite powder according to the invention.

The components according to the invention are favorably distinguished by the following properties:
excellent surface quality,
excellent surface nature,
excellent component density, preferably greater than 95%, in particular greater than 97%,
excellent shrinkage behavior,
excellent dimensional stability,
very few imperfections,
very relatively low porosity,
very low content of degradation products,
excellent three-point bending strength, preferably greater than 60 MPa, particularly preferably greater than 65 MPa, in particular greater than 70 MPa,
excellent elastic modulus, preferably 3420 $N/mm^2$, particularly preferably greater than 3750 $N/mm^2$, favorably greater than 4000 $N/mm^2$, in particular greater than 4500 $N/mm^2$,
excellent pH stability,
excellent biological compatibility,
excellent biocompatibility,
excellent osteoconduction,
excellent resorbability,
excellent biodegradability.

A thermoplastic further processing of the composite particles according to the invention usually brings about an at least partial fusion of the composite particles as a result of the partial or full melting of the polymer present therein. Preferably, said thermoplastic further processing does not lead, however, to a homogeneous distribution of the small particles or fragments thereof on the surface or in the interior of the now fused polymer, especially since the calcium carbonate particles preferably do not partially or fully melt under the conditions of further processing. Therefore, the resultant components preferably have a comparable inhomogeneity with regard to the distribution of the small particles or fragments thereof on the surface or in the interior of the now fused large particles when the size of the further processed composite particles is used as the size scale for the assessment.

The invention also provides the sphere-shaped calcium carbonate particles which can advantageously be used to produce the composite particles according to the invention, and the use thereof.

Thus, the present invention also concerns sphere-shaped calcium carbonate particles which are obtainable by means of a method in which
a. a calcium hydroxide suspension is initially charged,
b. carbon dioxide or a carbon dioxide-containing gas mixture is introduced into the suspension from step a. and
c. resultant calcium carbonate particles are separated off, with 0.3% by weight to 0.7% by weight of at least one aminotrisalkylenephosphonic acid being further added.

With regard to the preferred embodiment of said sphere-shaped calcium carbonate particles and preferred methods for their production, the above remarks apply mutatis mutandis.

Preferred application areas of the sphere-shaped calcium carbonate particles encompass their use as additive for paper, plastics, paints and/or varnishes, elastomers as well as adhesives and sealants, in construction chemistry, in dry mortar and in medical technology, especially as additive in resorbable polymers.

In this connection, what can be observed mutatis mutandis especially for compositions comprising, based in each case on the total weight of the composition,
a) at least 0.1% by weight, preferably at least 0.2% by weight and in particular at least 0.5% by weight to 50.0% by weight of at least one sphere-shaped calcium carbonate and
b) at least 0.1% by weight, preferably at least 0.2% by weight and in particular at least 0.5% by weight to 50.0% by weight of at least one polymer, preferably at least one thermoplastic polymer, particularly preferably at least one resorbable polymer and in particular at least one poly-D-, poly-L- and/or poly-D-L-lactic acid, are the advantages and effects mentioned in this application, especially with regard to the improvement of the mechanical properties and the acid stability of the composition. With regard to the preferred choice of polymer, the above remarks apply mutatis mutandis.

The present invention will be further illustrated below by means of multiple examples and comparative examples, without the intention of restricting the inventive concept as a result.

Materials used:
Granulate 1 (poly(L-lactide); inherent viscosity: 0.8-1.2 dL/g (0.1% in chloroform, 25° C.); Tg: 60-65° C.; Tm: 180-185° C.)
Granulate 2 (poly(L-lactide); inherent viscosity: 1.5-2.0 dL/g (0.1% in chloroform, 25° C.)); Tg: 60-65° C.;
Granulate 3 (poly(D,L-lactide); inherent viscosity: 1.8-2.2 dL/g (0.1% in chloroform, 25° C.)); Tg: 55-60° C.; amorphous polymer without melting point The average particle diameter of the polylactide granulates 1 to 3 was, in each case, within the range from 1 to 6 mm.

Within the context of the present examples, the following variables were ascertained as follows:
$CaCO_3$ content: The $CaCO_3$ content was ascertained by means of thermogravimetry with an STA 6000 from Perkin Elmer under nitrogen within the range from 40° C. to 1000° C. at a heating rate of 20° C./min. In this connection, the weight loss was determined between about 550° C. and 1000° C. and the $CaCO_3$ content in percent was calculated therefrom via a factor of 2.274 ($CaCO_3:CO_2$ molar mass ratio).

β-tricalcium phosphate content (β-TCP content): The β-TCP content was ascertained by means of thermogravimetry with an STA 6000 from Perkin Elmer under nitrogen within the range from 40° C. to 1000° C. at a heating rate of 20° C./min. The proportion by weight that remains at 1000° C. corresponds to the β-TCP content in percent.

$T_P$: The peak temperature $T_P$ was ascertained by means of thermogravimetry with an STA 6000 from Perkin Elmer under nitrogen within the range from 40° C. to 1000° C. at a heating rate of 20° C./min. The peak temperature of the first derivation of the mass loss curve corresponds to the temperature with the greatest mass loss in polymer degradation.

$d_{20}$, $d_{50}$, $d_{90}$: The particle-size distribution of the calcium carbonate-containing composite powder was determined using laser diffraction (HELOS measurement range R5 with RODOS dispersion system from Sympatec). For the calcium carbonate powder, the particle-size distribution was determined using the Sedigraph 5100 with MasterTech 51 from Micromeretics. The dispersion solution used was 0.1% sodium polyphosphate solution (NPP).

Fraction<20 μm: Determination as for $d_{50}$. Evaluation of the fraction <20 μm.

Moisture: The water content of the calcium carbonate-containing composite powder was determined using a Karl Fischer coulometer C30 from Mettler Toledo at 150° C. The water content of the calcium carbonate powder was determined using the halogen moisture analyzer HB43 from Mettler at 130° C. (amount weighed: 6.4-8.6 g of powder; measurement time: 8 minutes).

Inherent viscosity: Inherent viscosity (dL/g) was determined using an Ubbelohde viscometer, capillary 0c, in chloroform at 25° C. and 0.1% polymer concentration.

Flowability: The flowability of the samples was assessed using an electromotive film applicator from Erichsen. To this end, a 200 μm or 500 μm doctor blade was used. The application rate on film type 255 (Leneta) was 12.5 mm/s. The assessment was as follows: 1=very good; 2=good; 3=satisfactory; 4=adequate; 5=inadequate Determination of the mechanical properties on injection-molded test pieces: Three-point bending strength and elastic modulus were determined by means of the texture analyzer TA.XTplus (Stable Micro Systems, Godalming (UK)). The capacity of the load cell used was 50 kg. Exponent 6.1.9.0 software was used. The measurement details are presented in Table 1 below:

TABLE 1

| | |
|---|---|
| Stress device: | Three-point stress in accordance with DIN EN 843-1 Diameter of support/stress rolls: 5.0 mm |
| Measurement: | In accordance with DIN EN ISO 178 Support distance: 45.0 mm Test speed: 0.02 mm/s Preliminary speed: 0.03 mm/s Recording of force and distance |
| Test pieces: | Dimensions approx. 3 mm × 10 mm × 50 mm after production (injection-molding) Storage until measurement in desiccator at room temperature n ≥ 5 |

Test pieces were produced using the extruder HAAKE MiniLab II, or injection-molding using the HAAKE MiniJet II. The process conditions in relation to test-piece production are outlined in Table 2 below:

TABLE 2

| Composite | Temperature, extruder [° C.] | Temperature, injection-molding [° C.] | Temperature, injection mold [° C.] | Pressure, injection-molding [bar] | Time, injection-molding [s] |
|---|---|---|---|---|---|
| Example 3 | 180 | 180 | 80 | 700 | 10 |
| Example 4 | 180 | 180 | 70 | 700 | 10 |
| Example 5 | 185 | 185 | 80 | 700 | 10 |
| Example 6 | 195 | 195 | 80 | 700 | 10 |
| Example 7 | 175 | 175 | 72 | 700 | 10 |
| Comparison 1 | 175 | 175 | 70 | 700 | 10 |

Cytotoxicity Test

The cytotoxicity test (FDA/GelRed) was carried out as follows: The reference or negative control used was tissue culture polystyrene (TCPS). 4 replicates per sample and four TCPS (4×) as control were used in each case.

Experimental Procedure:
1. The unsterile samples were provided in a 24-well microtiter plate. In said plate, the samples and the TCPS platelets were sterilized with 70% ethanol (undenatured) for 30 min, then rinsed with 1×PBS (phosphate-buffered saline solution) for 2×30 min, and subsequently equilibrated with sterile α-medium. Thereafter, the samples were inoculated with MC3T3-E1 cells at an inoculation density of 25 000 cells/cm$^2$ (50 000 cells/ml).

A partial medium exchange (1:2) was performed on day 2.

2. After 1 day and 4 days in cell culture, cytotoxicity was determined.
3. Viability staining was performed on day 1 and 4 according to the standard protocol by means of a combination stain composed of FDA and GelRed.
4. The micrographs were generated on the Observer Z1m/LSM 700.
   Objective: EC Plan-Neofluar 10×;
   Images photographed with AxioCam HRc camera:
   Excitation of green fluorescence: LED Colibri 470; filter set FS10 (AF488)
   Excitation of red fluorescence: LED Colibri 530; filter set FS14 (AF546)
   Images captured in laser-scanning mode:
   Track 1: Laser: 488 nm, DBS 560 nm, PMT1: 488-560 nm,
   Track 2: Laser: 555 nm, DBS 565 nm, PMT2: 565-800 nm
5. The assessment was made according to the following cytotoxicity scale:
   Acceptance: the material is not cytotoxic (max. 5% dead cells)
   Slight inhibition: the material is slightly toxic (5%-20% dead cells)
   Distinct inhibition: the material is moderately toxic (20%-50% dead cells)
   Toxicity: the material is highly cytotoxic (>50%-100% dead cells)
6. The cell counts are based on the section of image that was photographed or scanned.
   The results are outlined in Table 3.
   Electron Microscope (SEM)
   The scanning electron micrographs were obtained using a high-voltage electron microscope (Zeiss, DSM 962) at 15 kV. The samples were sprayed with a gold/palladium layer.

EXAMPLE 1 (REACTANT FOR COMPOSITE POWDER ACCORDING TO THE CLAIMED INVENTION)

At a starting temperature of 10° C., a $CO_2$ gas mixture containing 20% $CO_2$ and 80% $N_2$ was introduced into a 4 L calcium hydroxide suspension having a concentration of 75 g/L CaO. The gas flow rate was 300 L/h. The reaction mixture was stirred at 350 rpm and the reaction heat was dissipated during the reaction. Upon an abrupt drop in the conductance (drop of more than 0.5 mS/cm/min and decrease in the conductance by more than 0.25 mS/cm within 30 seconds), 0.7% aminotris(methylenephosphonic acid), based on CaO (as theoretical reference value), is added to the suspension. The reaction to yield the sphere-shaped calcium carbonate particles was completed when the reaction mixture was quantitatively carbonated to yield sphere-shaped calcium carbonate particles, the reaction mixture having then a pH between 7 and 9. In the present case, the reaction was completed after approximately 2 h and the reaction mixture had a pH of 7 at the end of the reaction.

The resultant sphere-shaped calcium carbonate particles were separated off and dried by conventional means. They had an average particle diameter of 12 μm. A typical SEM image is presented in FIG. 1.

EXAMPLE 2 (REACTANT FOR COMPOSITE POWDER ACCORDING TO THE CLAIMED INVENTION)

500 mL of demineralized water were initially charged in a 1000 mL beaker. 125 g of sphere-shaped calcium carbonate particles as per Example 1 were added under stirring and the resultant mixture was stirred for 5 min. 37.5 g of a 10% sodium metaphosphate $(NaPO_3)_n$ solution were added slowly and the resultant mixture was stirred for 10 min. 75.0 g of 10% phosphoric acid were added slowly and the resultant mixture was stirred for 20 h. The precipitate is separated off and dried overnight at 130° C. in a drying cabinet. The resultant sphere-shaped calcium carbonate particles likewise had an average particle diameter of 12 μm.

Figure 2:
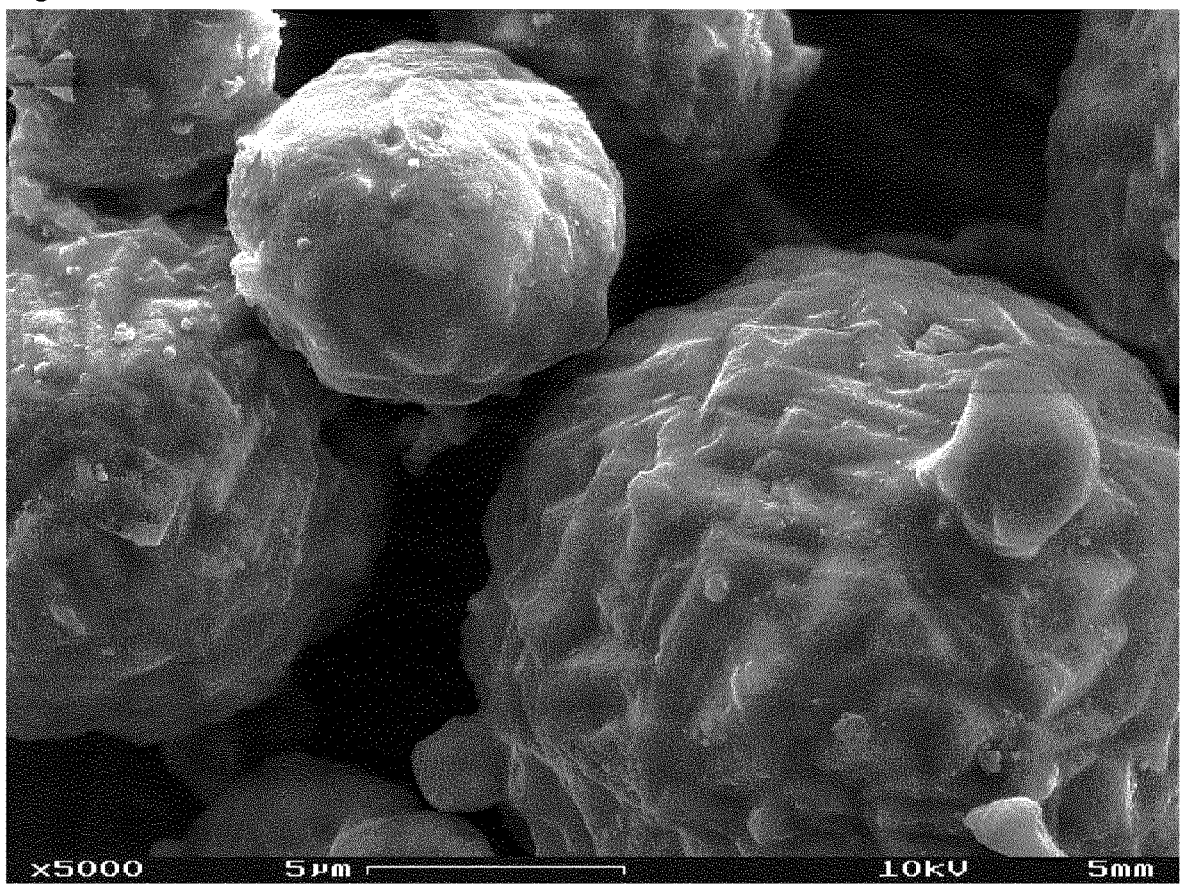
FIG. 2 show an SEM image of the sphere-shaped calcium carbonate particles. A thins phosphate layer can be identified on the surface of the sphere-shaped calcium carbonate particles.

An SEM image of the sphere-shaped calcium carbonate particles is presented in FIG. 2. A thin phosphate layer can be identified on the surface of the sphere-shaped calcium carbonate particles.

EXAMPLE 3 (COMPOSITE POWDER ACCORDING TO THE CLAIMED INVENTION)

A composite powder composed of sphere-shaped calcium carbonate particles and a polylactide (PLLA) was produced following the method described in JP 62083029 A, using the instrument NHS-1. Cooling was carried out using 12° C. cold water. A polylactide granulate 1 and the sphere-shaped calcium carbonate particles from Example 1 were used as the mother particles and as the baby particles (filler), respectively.

39.5 g of polylactide granulate were mixed with 26.3 g of $CaCO_3$ powder and filled at 6400 rpm. The rotor speed of the aggregate was adjusted to 6400 rpm (80 m/s) and the metered materials were processed for 10 min. The maximally reached temperature in the grinding space of the NHS-1 was 35° C. Altogether 7 repeats with the same amounts of material and same machine settings were carried out. Altogether 449 g of composite powder were obtained.

The composite powder obtained was manually dry-sieved through a 250 μm sieve. The sieve residue (fraction>250 μm) was 0.4%.

Figure 3A:
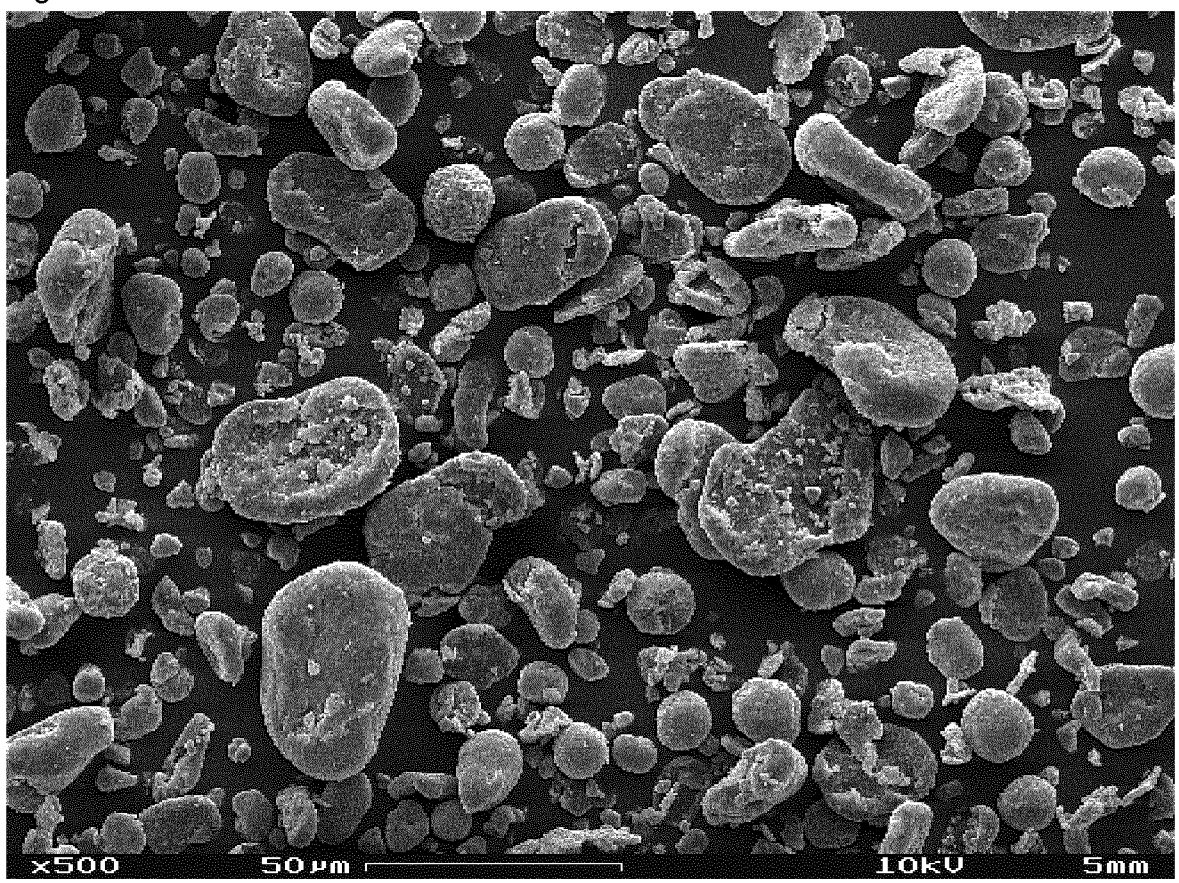
FIGS. 3a-3c show an SEM image from Example 3 as well as images of various doctor-blade applications (12.5 mm/s) from Example 3 (FIG. 3b: 200 μm doctor blade.

An SEM image of the composite powder obtained is presented in FIG. 3a.

Examples 4 to 7 (composite powder according to the claimed invention) Further composite powders were produced analogously to Example 3, though the cooling was carried out at approx. 20° C. in Example 5. 30 g of polylactide granulate were mixed with 20 g of $CaCO_3$ powder in each case. The maximally reached temperature in the grinding space of the NHS-1 was 33° C. for Example 4, 58° C. for Example 5, 35° C. for Example 6 and 35° C. for Example 7. The products were sieved in order to remove as far as possible the coarse fraction>250 μm (manual dry sieving through a 250 μm sieve). In Examples 4, 6 and 7, the fraction <20 μm was additionally removed as far as possible by flow classification (by means of air classification) or by sieving (by means of an air-jet sieving machine). The materials used, the production procedure with or without sieving/air classification and also the properties of the composite powders obtained are outlined in Table 3 below.

Figure 3B:
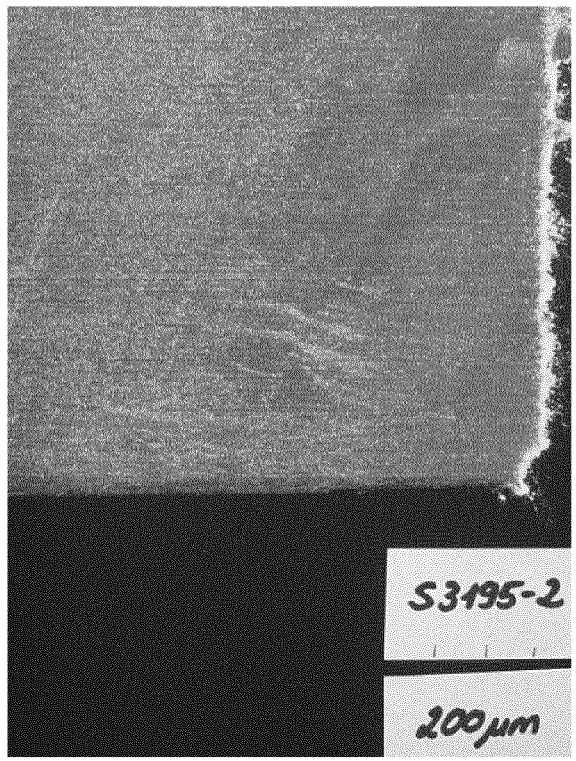
Figure 3C:

FIG. 3a, FIG. 3b and FIG. 3c show an SEM image from Example 3 as well as images of various doctor-blade applications (12.5 mm/s) from Example 3 (FIG. 3b: 200 μm doctor blade; FIG. 3c: 500 μm doctor blade).

The SEM image of the composite powder obtained is presented in FIG. 3a. In contrast to the edged, irregular particle shape typical for cryogenically ground powders, the particles of the composite powder obtained have a round particle shape or high sphericity that is very advantageous for SLM methods. The PLLA surface is sparsely occupied by sphere-shaped calcium carbonate particles and fragments thereof. The sample has a wide particle-size distribution with an increased fine fraction.

The powder is flowable to a limited extent (FIGS. 3b and 3c). A heap of powder is pushed ahead by the doctor blade. Owing to the limited flow behavior, presumably caused by a relatively high proportion of fine particles, only very thin layers are formed with both doctor blades.

Figure 4A:
FIGS. 4a-4c show an SEM image from Example 4 as well as images of various doctor-blade applications (12.5 mm/s) from Example 4 (FIG. 4b: 200 μm doctor blade.
Figure 4B:
Figure 4C:
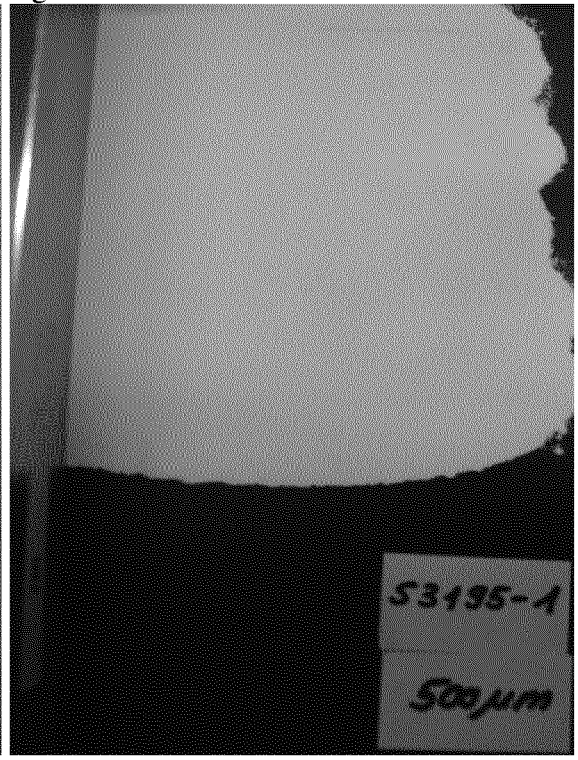

FIG. 4a, FIG. 4b and FIG. 4c show an SEM image from Example 4 as well as images of various doctor-blade applications (12.5 mm/s) from Example 4 (FIG. 4b: 200 μm doctor blade; FIG. 4c: 500 μm doctor blade).

The SEM image of the composite powder obtained is presented in FIG. 4a. In contrast to the edged, irregular particle shape typical for cryogenically ground powders, the particles of the composite powder obtained have a round particle shape or high sphericity that is very advantageous for SLM methods. The PLLA surface is sparsely occupied by sphere-shaped calcium carbonate particles and fragments thereof. The sample has a distinctly narrower particle-size distribution with little fine fraction.

The powder is very highly flowable and blade-coatable (FIGS. 4b and 4c). The thin layers (200 μm) can be blade-coated, too, and are largely free of doctor-blade stripes (grooves). The powder layer blade-coated at 500 μm is homogeneous, densely packed, smooth and free of doctor-blade stripes.

Figure 5A:
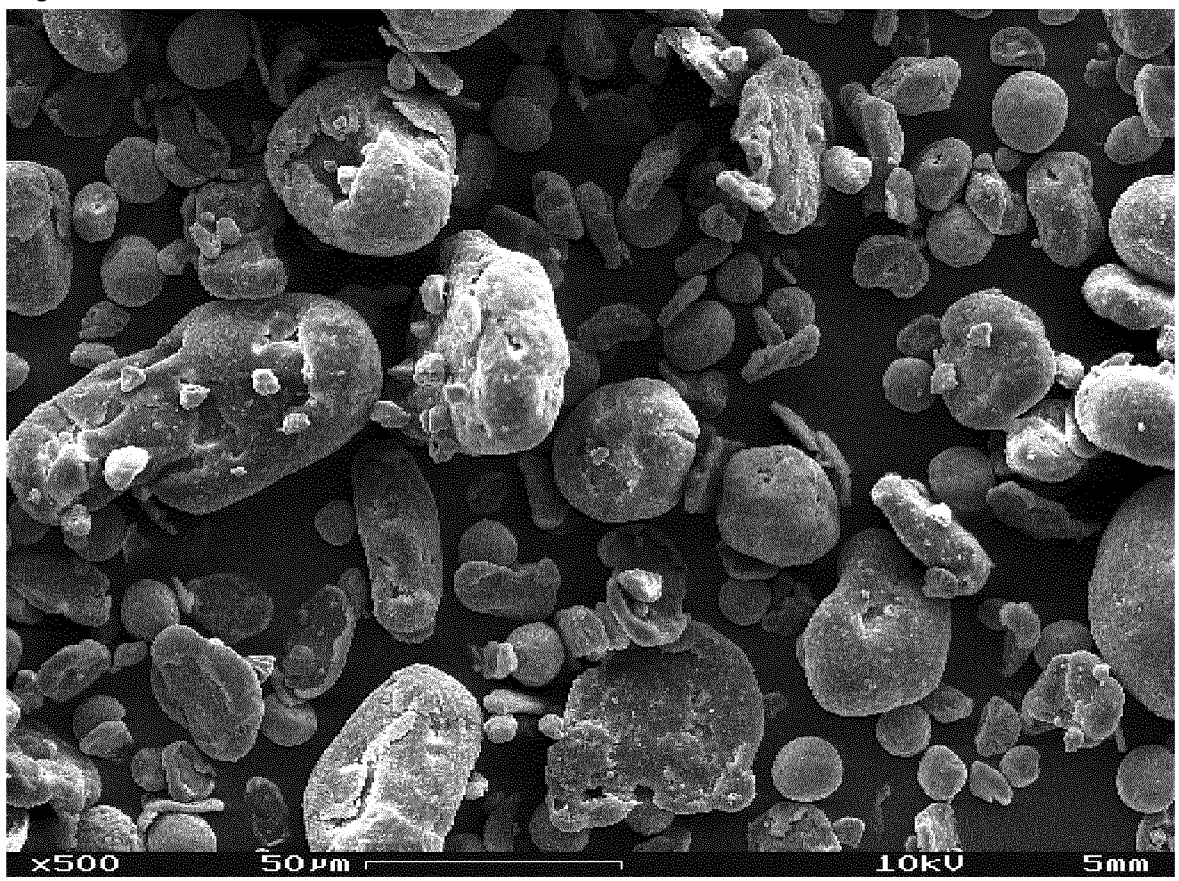
FIGS. 5a-5c show an SEM image from Example 5 as well as images of various doctor-blade applications (12.5 mm/s) from Example 5 (FIG. 5b: 200 μm doctor blade.
Figure 5B:
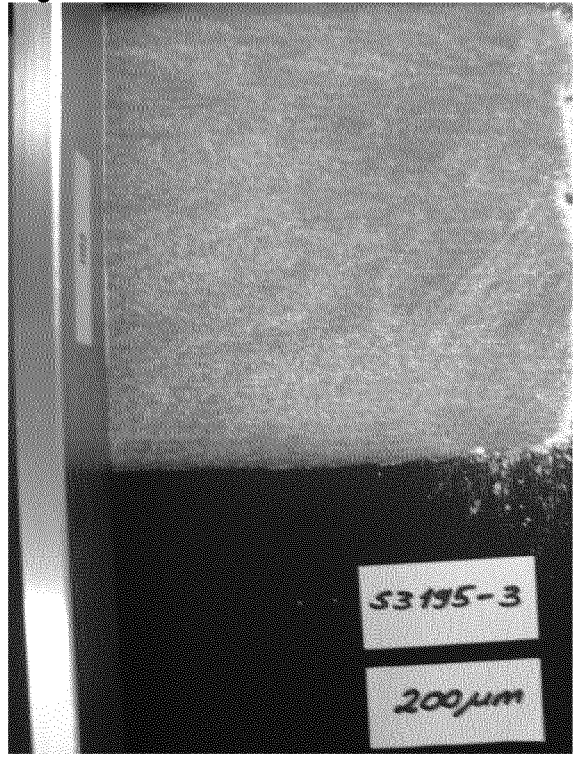
Figure 5C:

FIG. 5a, FIG. 5b and FIG. 5c show an SEM image from Example 5 as well as images of various doctor-blade applications (12.5 mm/s) from Example 5 (FIG. 5b: 200 μm doctor blade; FIG. 5c: 500 μm doctor blade). The powder is flowable to a limited extent. A heap of powder is pushed ahead by the doctor blade. Owing to the limited flow behavior, presumably caused by a relatively high proportion of fine particles, only very thin layers are formed with both doctor blades.

Figure 6A:
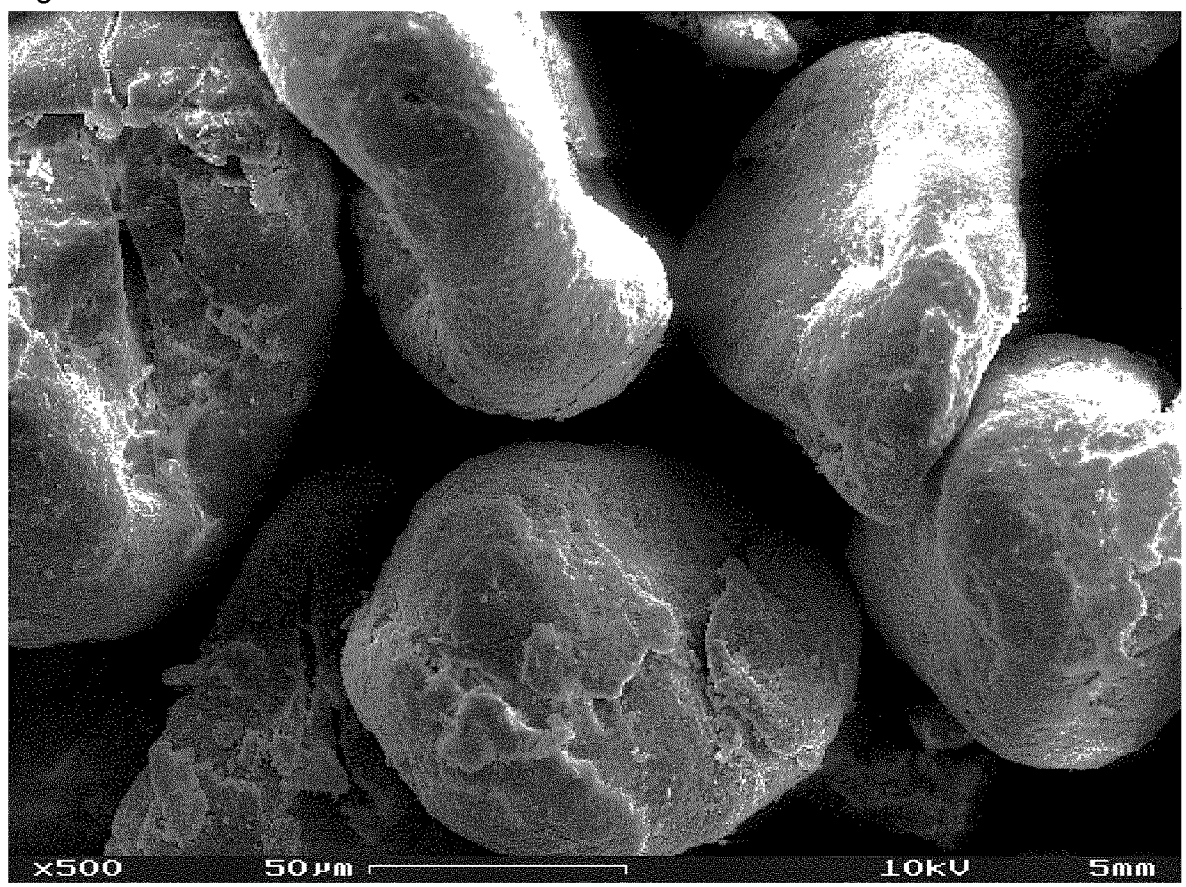
FIGS. 6a-6c show an SEM image from Example 6 as well as images of various doctor-blade applications (12.5 mm/s) from Example 6 (FIG. 6b: 200 μm doctor blade.
Figure 6B:
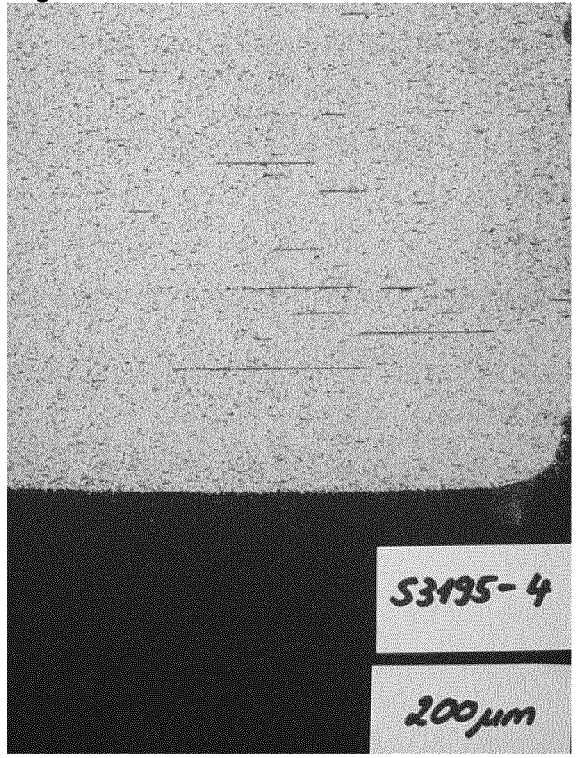
Figure 6C:
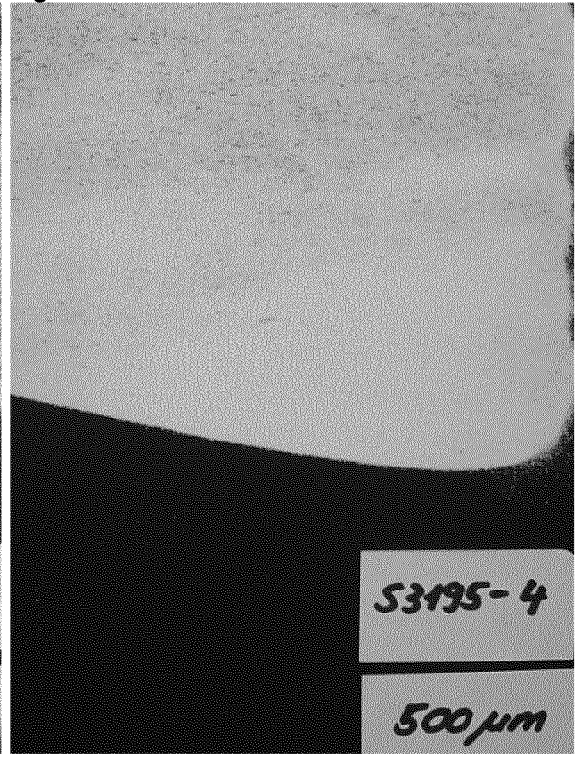

FIG. 6a, FIG. 6b and FIG. 6c show an SEM image from Example 6 as well as images of various doctor-blade applications (12.5 mm/s) from Example 6 (FIG. 6b: 200 μm doctor blade; FIG. 6c: 500 μm doctor blade). The powder is highly flowable and blade-coatable. The thin layers (200 μm) can be blade-coated, too. Individual doctor-blade stripes presumably due to excessively coarse powder particles are identifiable. The powder layer blade-coated at 500 μm is not quite densely packed, but is free of doctor-blade stripes.

Figure 7A:
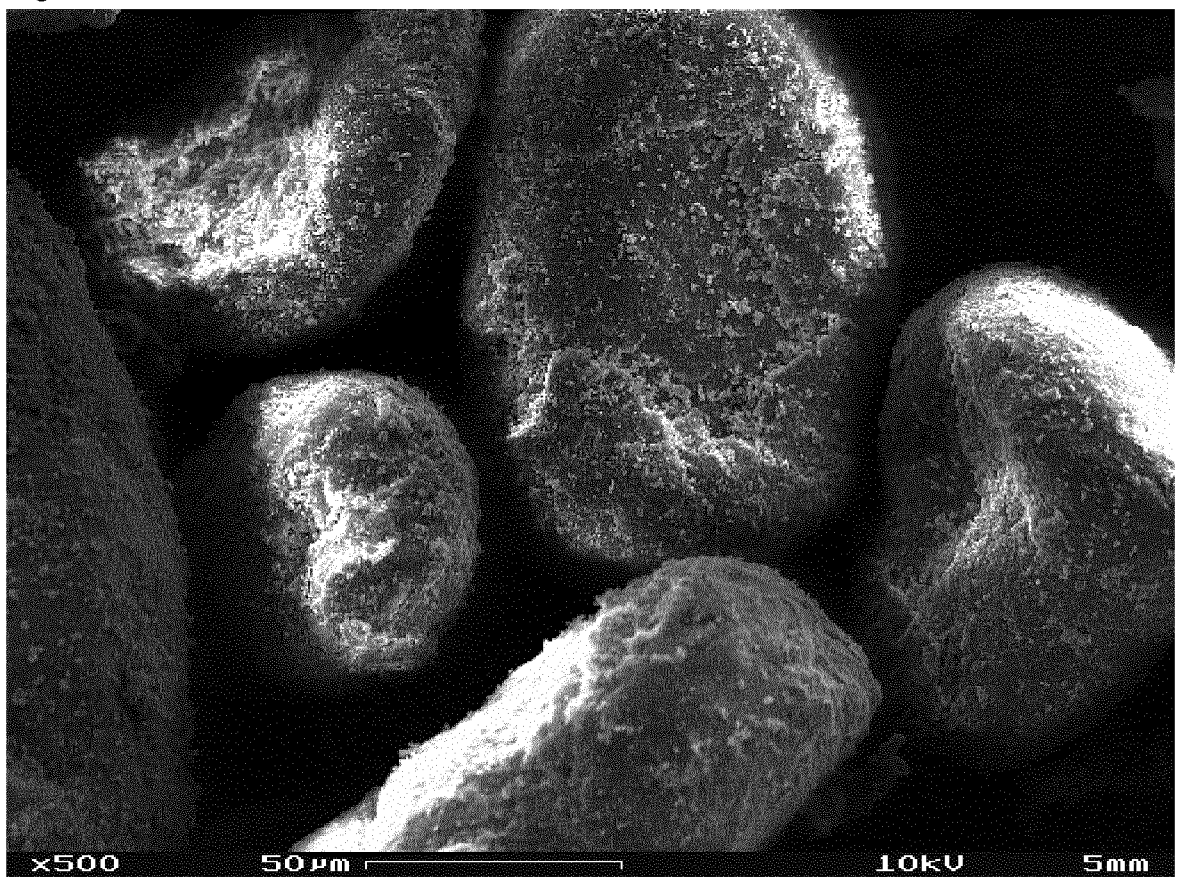
FIGS. 7a-7c show an SEM image from Example 7 as well as images of various doctor-blade applications (12.5 mm/s) from Example 7 (FIG. 7b: 200 μm doctor blade.
Figure 7B:
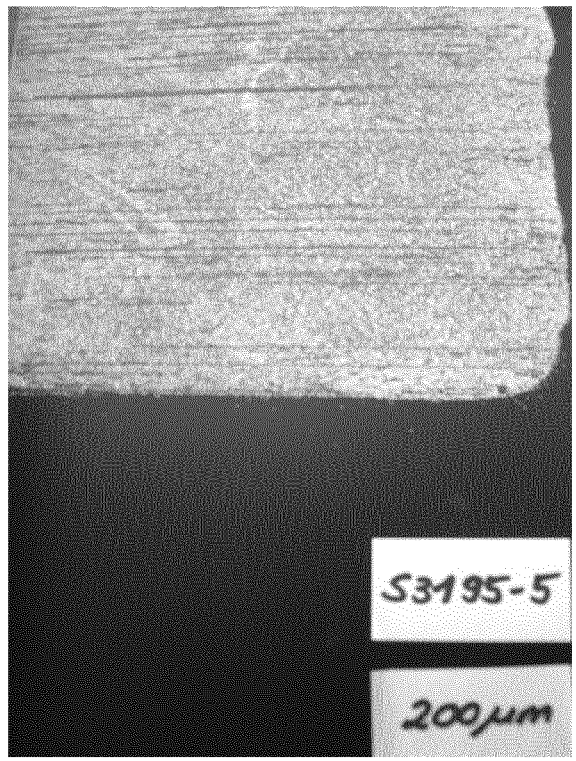
Figure 7C:
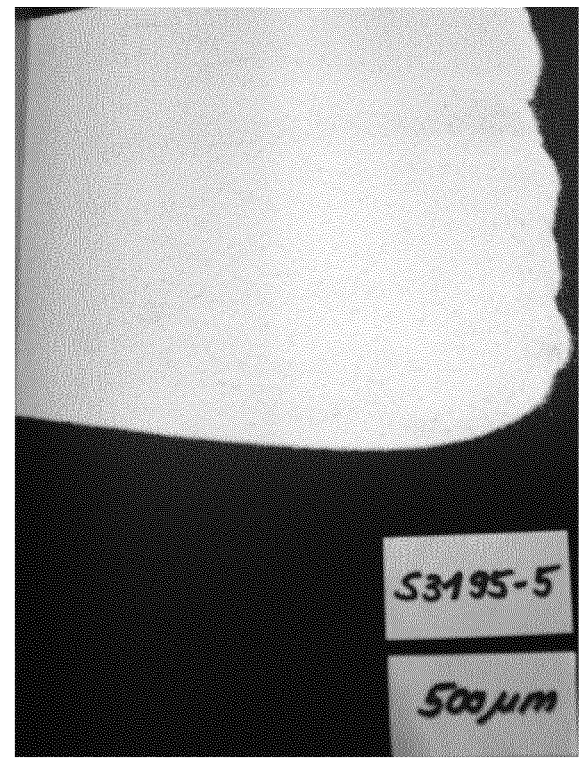

FIG. 7a, FIG. 7b and FIG. 7c show an SEM image from Example 7 as well as images of various doctor-blade applications (12.5 mm/s) from Example 7 (FIG. 7b: 200 μm doctor blade; FIG. 7c: 500 μm doctor blade). The powder is flowable and blade-coatable. The thin layers (200 μm) can be blade-coated, too. They are not homogeneous and there are more doctor-blade stripes. Somewhat limited flow behavior is presumably caused by excessively coarse powder particles. The powder layer blade-coated at 500 μm is homogeneous and free of doctor-blade stripes.

Comparison 1 (Comparative Example)

Microstructured composite particles composed of sphere-shaped calcium carbonate particles from Example 1 and an amorphous polylactide (PDLLA) were produced following the method described in JP 62083029 A, using the instrument NHS-1. Cooling was carried out using 12° C. cold water. A polylactide granulate 3 and the sphere-shaped calcium carbonate particles from Example 1 were used as the mother particles and as the baby particles, respectively.

39.5 g of polylactide granulate were mixed with 10.5 g of $CaCO_3$ powder and filled at 8000 rpm. The rotor speed of the aggregate was adjusted to 8000 rpm (100 m/s) and the metered materials were processed for 1.5 min. The maximally reached temperature in the grinding space of the NHS-1 was 71° C. Altogether 49 repeats with the same amounts of material and same machine settings were carried out. Altogether 2376 g of structured composite particles were obtained. The structured composite particles obtained were manually dry-sieved through a 800 μm sieve for the measurement of the particle-size distribution. The sieve residue (fraction>800 μm) was 47%.

The properties of the microstructured composite particles obtained are outlined in Table 3 below.

Figure 8A:
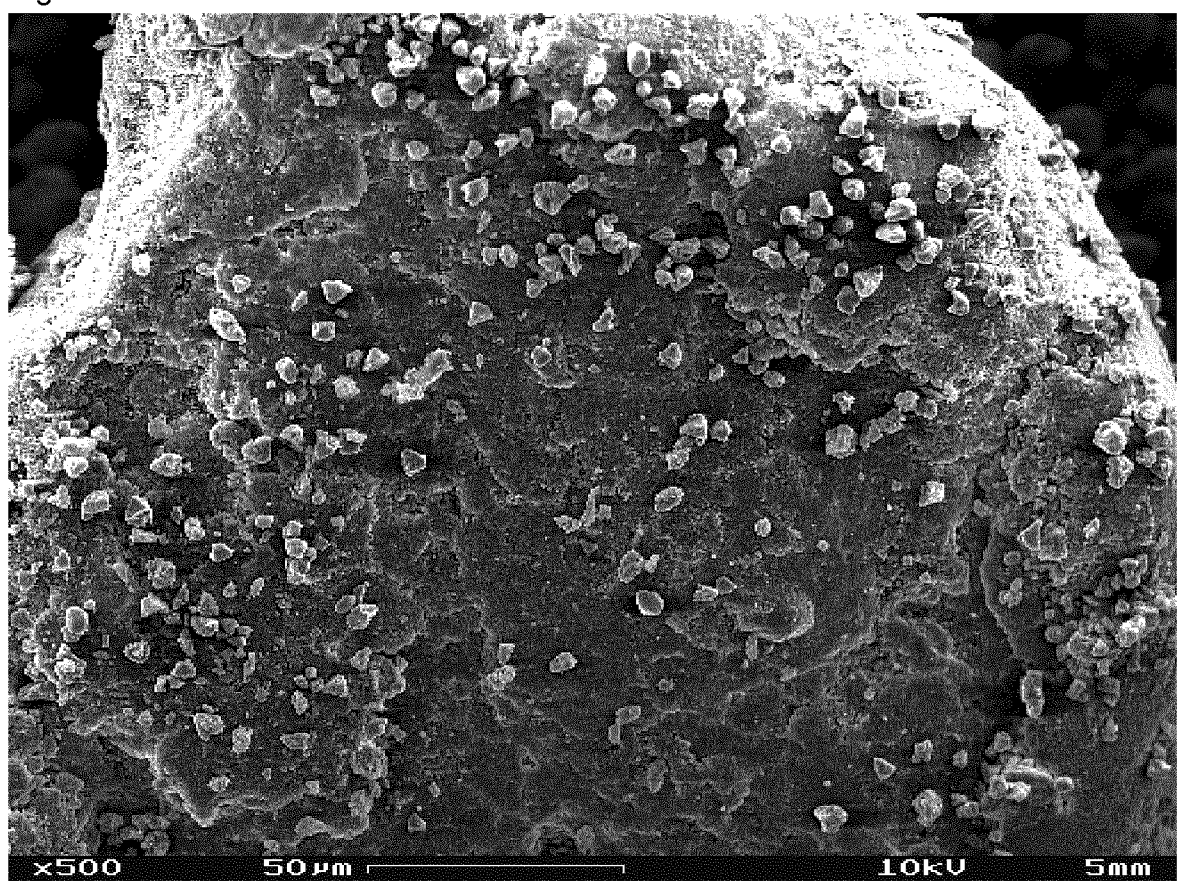
FIGS. 8a-8c show an SEM image from Comparison 1 as well as images of various doctor-blade applications (12.5 mm/s) from Comparison 1 (FIG. 8b: 200 μm doctor blade.
Figure 8B:
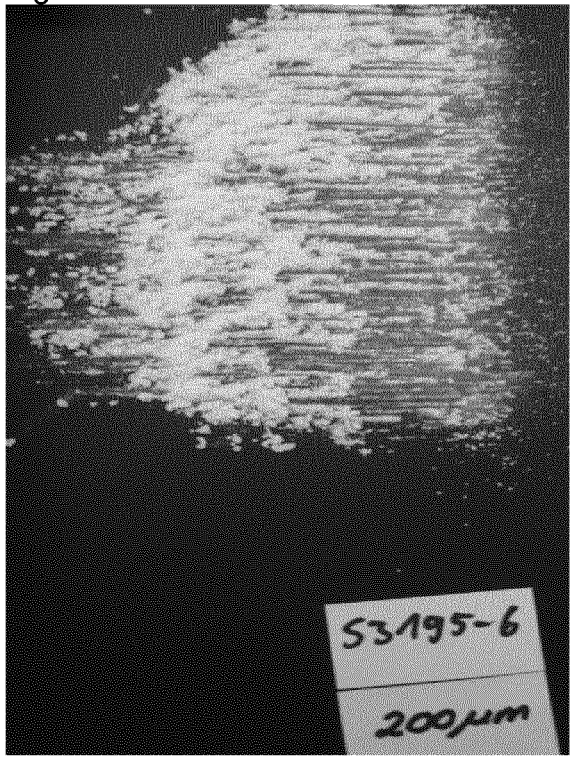
Figure 8C:
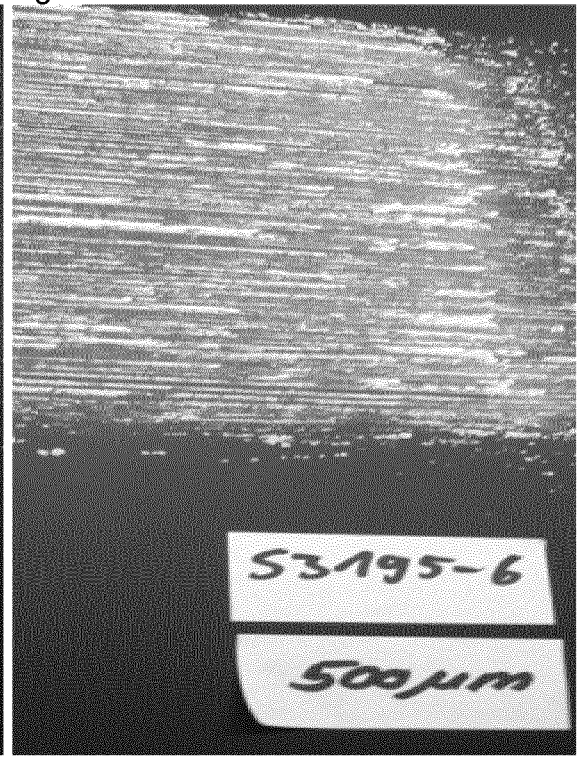

FIG. 8a, FIG. 8b and FIG. 8c show an SEM image from Comparison 1 as well as images of various doctor-blade applications (12.5 mm/s) from Comparison 1 (FIG. 8b: 200 μm doctor blade; FIG. 8c: 500 μm doctor blade). The powder is poorly flowable and cannot be blade-coated to form layer thicknesses 200 or 500 μm thin. The excessively coarse, irregular particles become stuck during blade-coating. What arise are inhomogeneous layers with highly frequent and pronounced doctor-blade stripes.

The SEM analysis shows that the surfaces of the structured composite powders are sparsely occupied by sphere-shaped calcium carbonate particles and fragments thereof. In comparison with Examples 3-7, the particles have a more irregular particle geometry.

EXAMPLE 8 (COMPOSITE POWDER ACCORDING TO THE CLAIMED INVENTION)

Figure 9A:
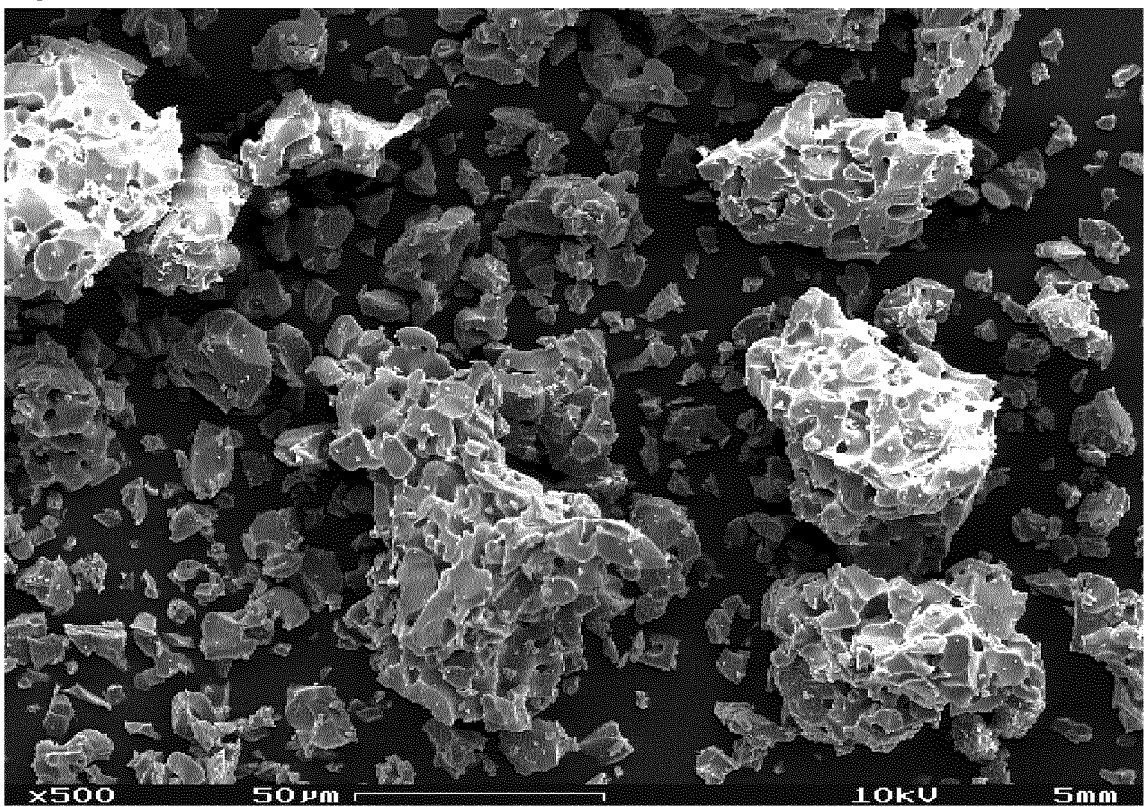
FIGS. 9a-9b show an SEM image of β-tricalcium phosphate (β-TCP).
Figure 9B:
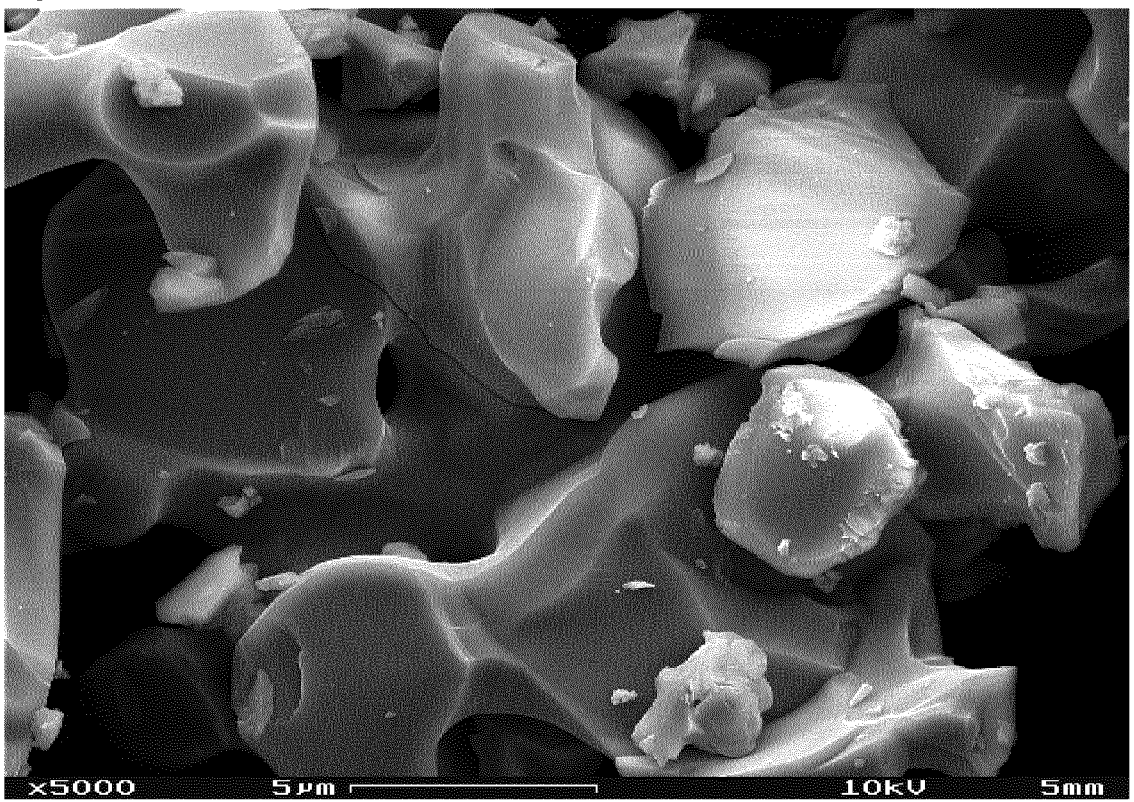

A composite powder composed of β-tricalcium phosphate particles and a polylactide (PDLLA) was produced following the method described in JP 62083029 A, using the instrument NHS-1. Cooling was carried out using 12° C. cold water. A polylactide granulate 3 and β-tricalcium phosphate (β-TCP; $d_{20}$=30 µm; $d_{50}$=141 µm; $d_{90}$=544 µm) were used as the mother particles and as the baby particles, respectively. The SEM image of the β-TCP used are shown in FIG. 9a and FIG. 9b.

30.0 g of polylactide granulate were mixed with 20.0 g of β-TCP powder and filled at 6400 rpm. The rotor speed of the aggregate was adjusted to 6400 rpm (80 m/s) and the metered materials were processed for 10 min. Altogether 5 repeats with the same amounts of material and same machine settings were carried out. Altogether 249 g of composite powder were obtained. The product were sieved in order to remove as far as possible the coarse fraction>250 µm (manual dry sieving through a 250 µm sieve). Thereafter, the fine fraction <20 µm was separated off by means of an air-jet sieving machine via a 20 µm sieve.

EXAMPLE 9 (COMPOSITE POWDER ACCORDING TO THE CLAIMED INVENTION)

A composite powder composed of rhombohedral calcium carbonate particles and a polylactide (PDLLA) was produced following the method described in JP 62083029 A, using the instrument NHS-1. Cooling was carried out using 12° C. cold water. A polylactide granulate 3 and rhombohedral calcium carbonate particles ($d_{20}$=11 µm; $d_{50}$=16 µm; $d_{90}$=32 µm) were used as the mother particles and as the baby particles, respectively.

30.0 g of polylactide granulate were mixed with 20.0 g of the rhombohedral calcium carbonate particles and filled at 6400 rpm. The rotor speed of the aggregate was adjusted to 6400 rpm (80 m/s) and the metered materials were processed for 10 min. Altogether 5 repeats with the same amounts of material and same machine settings were carried out. Altogether 232 g of composite powder were obtained. The product were sieved in order to remove as far as possible the coarse fraction>250 µm (manual dry sieving through a 250 µm sieve). Thereafter, the fine fraction <20 µm was separated off by means of an air-jet sieving machine via a 20 µm sieve.

EXAMPLE 10 (COMPOSITE POWDER ACCORDING TO THE CLAIMED INVENTION)

A composite powder composed of ground calcium carbonate particles and a polylactide (PDLLA) was produced following the method described in JP 62083029 A, using the instrument NHS-1. Cooling was carried out using 12° C. cold water. A polylactide granulate 3 and ground calcium carbonate (GCC; $d_{20}$=15 µm; $d_{50}$=46 µm; $d_{90}$=146 µm) were used as the mother particles and as the baby particles, respectively.

30.0 g of polylactide granulate were mixed with 20.0 g of GCC and filled at 6400 rpm. The rotor speed of the aggregate was adjusted to 6400 rpm (80 m/s) and the metered materials were processed for 10 min. Altogether 5 repeats with the same amounts of material and same machine settings were carried out. Altogether 247 g of composite powder were obtained. The product were sieved in order to remove as far as possible the coarse fraction>250 µm (manual dry sieving through a 250 µm sieve). Thereafter, the fine fraction <20 µm was separated off by means of an air-jet sieving machine via a 20 µm sieve.

TABLE 3

| | Example 3 | Example 4 | Example 5 | Example 6 | Example 7 | Comparison 1 |
|---|---|---|---|---|---|---|
| Composition for the production of the composite powder comprising microstructured particles | | | | | | |
| m(Example 1) [% by weight] | 40 | 40 | 0 | 40 | 40 | 20 |
| m(Example 2) [% by weight] | 0 | 0 | 40 | 0 | 0 | 0 |
| Polylactide | Granulate 1 | Granulate 1 | Granulate 1 | Granulate 2 | Granulate 3 | Granulate 3 |
| m(Polylactide) [% by weight] | 60 | 60 | 60 | 60 | 60 | 80 |
| Production of the composite powder comprising microstructured particles | | | | | | |
| Sieving | <250 µm | <250 µm <20 µm (air classification) | <250 µm | <250 µm <20 µm (air-jet sieving) | <250 µm <20 µm (air-jet sieving) | <800 µm (only for measurement of the particle-size distribution) |
| $CaCO_3$ content [% by weight][1] | 41.0 | 22.4 | 35.0 | 19.5 | 22.3 | 22.4 (average from 5 measurements) |
| $T_P$ [° C.][1] | 291 | 310 | 341 | 304 | 286 | 319 (average from 5 measurements) |
| $d_{50}$ [µm][1] | 25 | 47 | 26 | 112 | 136 | 228 |
| Fraction < 20 µm [% by volume][1] | 43.6 | 13.7 | 37.7 | 0.3 | 2.3 | 20.6 |
| $d_{20}$ [µm][1] | 9 | 26 | 14 | 69 | 80 | |
| $d_{90}$ [µm][1] | 86 | 102 | 70 | 223 | 247 | |
| $d_{20}/d_{50}$ [%] | 36 | 52 | 54 | 62 | 59 | |
| Moisture [% by weight][1] | 0.8 | 0.6 | 0.5 | 0.9 | 0.9 | 0.3 |
| Inherent viscosity [dL/g] | 1.0 | 1.0 | 0.9 | 1.9 | 1.9 | 1.9 |

TABLE 3-continued

| | | | | | | |
|---|---|---|---|---|---|---|
| Three-point bending strength [MPa] | 66 | 68 | 77 | 84 | 67 | 79 |
| Elastic modulus [N/mm$^2$] | 4782 | 3901 | 4518 | 3530 | 3594 | 3420 |
| Flowability | 4 | 1 | 4 | 2 | 3 | 5 |
| Cytotoxicity test | not cytotoxic | not cytotoxic | not cytotoxic | — | not cytotoxic | not cytotoxic |

| | Example 8 | Example 9 | Example 10 |
|---|---|---|---|
| Composition for the production of the composite powder comprising microstructured particles | | | |
| m(Filler) [% by weight] | 40 | 40 | 40 |
| Polylactide | Granulate 3 | Granulate 3 | Granulate 3 |
| m(Polylactide) [% by weight] | 60 | 60 | 60 |
| Production of the composite powder comprising microstructured particles | | | |
| Sieving | <250 µm <20 µm Air-jet sieving | <250 µm <20 µm Air-jet sieving | <250 µm <20 µm Air-jet sieving |
| Filler content [% by weight]* | 24.9 | 24.2 | 26.6 |
| $T_P$ [° C.] | 341° C. | 303° C. | 303° C. |
| $d_{20}$ [µm] | 85 | 74 | 75 |
| $d_{50}$ [µm] | 131 | 128 | 120 |
| $d_{90}$ [µm] | 226 | 257 | 230 |
| Fraction < 20 µm [% by volume] | 3.0 | 4.5 | 1.6 |
| Moisture [% by weight] | 0.6 | 0.6 | 0.6 |
| Inherent viscosity [dL/g] | 1.8 | 1.8 | 1.9 |

[1]at least duplicate determination

Comparison 2, Example 11 (composite powder according to the claimed invention), Example 12 (composite powder according to the claimed invention), Example 13 (composite powder according to the claimed invention), Example 14 (composite powder according to the claimed invention) and Example 15 PLA pellets were mixed and melted as pure pellets and with 4 different fillers (25% by weight) using a Brabender Plasti-Corder. The chamber temperature was 190° C. at a rotational speed of 50 rpm. Pellets and filler powder were mixed for 5 minutes; thereafter, approx. 16 g of the mixture were pressed in a hydraulic press at a pressure of 0.96-1.2 MPa for 5 minutes.

In all the examples, the polymer used was PLA (NatureWorks Ingeo TM Biopolymer 3251 D). In Comparison 2, no calcium carbonate particles were added. In Example 11, calcium carbonate particles according to Example 1 were added. In Example 12, calcium carbonate particles according to Example 2 were added. In Example 13, calcium carbonate particles were added, the particles having been produced analogously to Example 2 but without addition of phosphoric acid. In Example 14, calcium carbonate particles were added, the particles having been produced analogously to Example 2 but without addition of sodium metaphosphate (NaPO$_3$)$_n$). In Example 15, stearic acid-coated calcium carbonate particles obtained by conventional means were added.

Characterization of the PLA composites of Comparison 2 and Example 11-15 a) Mechanical properties

The mechanical properties of PLA and of the composites were tested using the universal testing machine UTM 1445 from Zwick/Roell. The tensile strength, the elastic modulus and the stretch of the materials were determined here. The test speed was 10 mm/min at a measurement length of 50 mm.

b) Thermal properties

The thermal stability of the samples was determined by means of thermogravimetry. The thermogravimetric measurements were carried out using an STA 6000 from Perkin Elmer under nitrogen within the range from 40° C. to 1000° C. at a heating rate of 20° C./min.

c) Optical assessment of the samples (**grades of 1-3)

1=transparent pure polymer; no identifiable discoloration due to thermal degradation 2=white polymer compound; change in color to white due to addition of the filler; no identifiable discoloration due to thermal degradation 3=brown color due to thermal degradation of the compound The addition of the CaCO$_3$ particles to the PLA matrix led to a change in color from transparent pure PLA to white composites for all the fillers except for Example 15. In the case of the sample with stearic acid-coated calcium carbonate particles, the color changed to a light brown, indicating polymer degradation. All the other samples show no signs of degradation at all.

The observed properties are outlined in Table 4.

TABLE 4

|  | Comparison 2 | Example 11 | Example 12 | Example 13 | Example 14 | Example 15 |
|---|---|---|---|---|---|---|
| CaCO$_3$ particles |  | Example 1 | Example 2 | Example 2 without addition of phosphoric acid | Example 2 without addition of sodium metaphosphate | Coated with stearic acid (1.0%) |
| pH [1] (immediately/24 h) |  | 10.0/10.0 | 6.1/6.2 | 8.9/9.0 | 7.0/7.0 | — |
| Moisture [%] |  | 0.1 | 0.1 | 0.1 | 0.1 | 0.1 |
| d$_{50}$ [μm] |  | 12.1 | 12.2 | 12.0 | 14.3 | 14.2 |
| Spec. surface area [m$^2$/g] |  | 1.1 | 0.2 | 0.6 | 0.9 | 4.9 |
| P$_2$O$_5$ content [%] |  | 0.3 | 3.1 | 0.4 | 6.8 | — |
| Qualitative phase analysis |  | Calcite | Calcite | Calcite | Calcite + brushite |  |
| Tensile strength [MPa] | 47.99 | 44.57 | 40.56 | 40.20 | 37.95 | 41.39 |
| Elastic modulus [MPa] | 1345.0 | 1680.4 | 1718.9 | 1601.9 | 1625.8 | 1627.1 |
| Onset temperature (TGA) [° C.] | 348.8 | 326.1 | 360.3 | 337.4 | 358.4 | 322.9 |
| Peak temperature (TGA) [° C.] | 377.6 | 356.5 | 380.3 | 368.1 | 380.8 | 354.5 |
| Grading of test pieces** | 1 | 2 | 2 | 2 | 2 | 3 |

The invention claimed is:

1. A composite powder containing microstructured particles in which large particles are combined with small particles, wherein
   the large particles have an average particle diameter within the range from 0.1 μm to 10 mm,
   the large particles comprise at least one polymer,
   the small particles are arranged on the surface of the large particles and/or distributed inhomogeneously within the large particles,
   the small particles comprise sphere-shaped precipitated calcium carbonate particles having an average diameter within the range from 0.05 μm to 50.0 μm,
   characterized in that
   the sphere-shaped calcium carbonate particles are obtained by a method in which
   a. a calcium hydroxide suspension is initially charged,
   b. carbon dioxide or a carbon dioxide-containing gas mixture is introduced into the suspension from step a. and
   c. resultant calcium carbonate particles are separated off, with 0.3% by weight to 0.7% by weight of at least one aminotrisalkylenephosphonic acid being further added, and
   the particles of the composite powder have an average particle size d$_{50}$ within the range from 10 μm to less than 200 μm.

2. The composite powder as claimed in claim 1, comprising calcium carbonate particles obtained by a method in which aminotrismethylenephosphonic acid, aminotrisethylenephosphonic acid, aminotrispropylenephosphonic acid and/or aminotrisbutylenephosphonic acid are added.

3. The composite powder as claimed in claim 1, comprising calcium carbonate particles obtainable by a method in which the carbon dioxide or the carbon dioxide-containing gas mixture is introduced until the reaction mixture has a pH less than 9.

4. The composite powder as claimed in claim 1, comprising calcium carbonate particles obtainable by a method in which the conversion of the calcium hydroxide suspension with the carbon dioxide or the carbon dioxide-containing gas mixture is carried out at a temperature less than 25° C.

5. The composite powder as claimed in claim 1, comprising calcium carbonate particles obtainable by a method in which carbon dioxide or a carbon dioxide-containing gas mixture is introduced into the calcium hydroxide suspension at a gas flow rate within the range from 0.02 L CO$_2$/(h*g Ca(OH)$_2$) to 2.0 L CO$_2$/(h*g Ca(OH)$_2$).

6. The composite powder as claimed in claim 1, characterized in that the sphere-shaped calcium carbonate particles have an average diameter less than 30.0 μm.

7. The composite powder as claimed in claim 1, characterized in that the sphere-shaped calcium carbonate particles have a size distribution in which at least 90.0% by weight of all calcium carbonate particles have a particle diameter within the range of average particle diameter −30% to average particle diameter +30%.

8. The composite powder as claimed in claim 1, characterized in that the sphere-shaped calcium carbonate particles have a shape factor, defined as the quotient formed from minimum particle diameter and maximum particle diameter, greater than 0.90.

9. The composite powder as claimed in claim 1, characterized in that the large particles comprise at least one thermoplastic polymer.

10. The composite powder as claimed in claim 1, characterized in that the large particles comprise at least one resorbable polymer.

11. The composite powder as claimed in claim 10, characterized in that the resorbable polymer has an inherent viscosity, measured in chloroform at 25° C. and 0.1% polymer concentration, within the range from 0.3 dL/g to 8.0 dL/g.

12. The composite powder as claimed in claim 1, characterized in that the large particles comprise poly-D-, poly-L- and/or poly-D,L-lactic acid.

13. The composite powder as claimed in claim 1, characterized in that the large particles comprise at least one resorbable polyester having a number-average molecular weight within the range from 500 g/mol to 1 000 000 g/mol.

14. The composite powder as claimed in claim 1, characterized in that the large particles comprise at least one polyamide.

15. The composite powder as claimed in claim 1, characterized in that the large particles comprise at least one polyurethane.

16. The composite powder as claimed in claim 1, characterized in that the proportion by weight of the precipitated calcium carbonate particles, based on the total weight of the composite powder, is at least 0.1% by weight.

17. The composite powder as claimed in claim 1, characterized in that the composite powder comprise, based on the total weight of the composite powder, 40.0% by weight to 80.0% by weight of a poly-L-lactic acid (PLLA) and 20.0% by weight to 60.0% by weight of precipitated calcium carbonate particles.

18. A method comprising adding a composite powder as claimed in claim 1 as additive, as additive substance or starting material for compounding, for the production of components, for applications in medical technology and/or in microtechnology and/or for the production of foamed articles.

19. A component obtainable by selective laser sintering of a composition comprising a composite powder as claimed in claim 1, except for implants for uses in the field of neurosurgery, oral surgery, jaw surgery, facial surgery, neck surgery, nose surgery, ear surgery, hand surgery, foot surgery, thorax surgery, rib surgery and shoulder surgery.

20. Sphere-shaped calcium carbonate particles obtained by a method in which
   a. a calcium hydroxide suspension is initially charged,
   b. carbon dioxide or a carbon dioxide-containing gas mixture is introduced into the suspension from step a. and
   c. resultant calcium carbonate particles are separated off, with 0.3% by weight to 0.7% by weight of at least one aminotrisalkylenephosphonic acid being further added.

21. A method comprising adding the sphere-shaped calcium carbonate particles as claimed in claim 20 as additive for paper, plastics, paints, varnishes, elastomers, adhesives, sealants, in construction chemistry, in dry mortar and in medical technology, or in resorbable polymers.

22. The composite powder as claimed in claim 1, characterized in that the sphere-shaped calcium carbonate particles have an average diameter less than 20.0 μm.

23. A method comprising adding a composite powder as claimed in claim 1 as polymer additive, as additive substance or starting material for compounding, for the production of components, for applications in medical technology and/or in microtechnology and/or for the production of foamed articles.

* * * * *